(12) United States Patent
Aklog et al.

(10) Patent No.: US 8,052,751 B2
(45) Date of Patent: *Nov. 8, 2011

(54) ANNULOPLASTY RINGS FOR REPAIRING CARDIAC VALVES

(75) Inventors: Lishan Aklog, Scarsdale, NY (US); Michael Reo, Redwood City, CA (US)

(73) Assignee: Flexcor, Inc., Redwood City, CA (US)

( * ) Notice: Subject to any disclaimer, the term of this patent is extended or adjusted under 35 U.S.C. 154(b) by 867 days.

This patent is subject to a terminal disclaimer.

(21) Appl. No.: 10/884,015

(22) Filed: Jul. 2, 2004

(65) Prior Publication Data

US 2005/0004668 A1 Jan. 6, 2005

Related U.S. Application Data

(63) Continuation-in-part of application No. 10/613,761, filed on Jul. 2, 2003, now abandoned.

(51) Int. Cl.
*A61F 2/24* (2006.01)
(52) U.S. Cl. .......... 623/2.36; 623/2.37; 606/56
(58) Field of Classification Search ............... 623/2.36, 623/2.37; 606/56
See application file for complete search history.

(56) References Cited

U.S. PATENT DOCUMENTS

| | | | | |
|---|---|---|---|---|
| 1,590,459 A | * | 6/1926 | Vondersaar | 408/104 |
| 4,006,740 A | * | 2/1977 | Volkov et al. | 606/53 |
| 4,042,979 A | * | 8/1977 | Angell | 623/2.37 |
| 4,784,125 A | * | 11/1988 | Monticelli et al. | 606/56 |
| 5,306,296 A | * | 4/1994 | Wright et al. | 623/2.37 |
| 5,593,424 A | | 1/1997 | Northrup, III | |
| 5,676,697 A | * | 10/1997 | McDonald | 623/1.35 |
| 5,716,397 A | * | 2/1998 | Myers | 623/2.36 |
| 5,749,825 A | * | 5/1998 | Fischell et al. | 600/3 |
| 5,971,984 A | * | 10/1999 | Taylor et al. | 606/54 |
| 6,102,945 A | | 8/2000 | Campbell | |
| 6,210,429 B1 | * | 4/2001 | Vardi et al. | 623/1.11 |
| 6,210,432 B1 | | 4/2001 | Solem et al. | |
| 6,325,826 B1 | * | 12/2001 | Vardi et al. | 623/1.35 |
| 6,332,893 B1 | | 12/2001 | Mortier et al. | |
| 6,419,695 B1 | | 7/2002 | Gabbay | |
| 6,723,038 B1 | | 4/2004 | Schroeder et al. | |

(Continued)

FOREIGN PATENT DOCUMENTS

WO WO 87/05489 9/1987

(Continued)

OTHER PUBLICATIONS

English language translation of German language patent WO98/18411 to Mahmoodi (of record).*

*Primary Examiner* — Paul Prebilic
(74) *Attorney, Agent, or Firm* — Greenberg Traurig, LLP; Chinh H. Pham; Roman Fayerberg

(57) ABSTRACT

Implantable devices and methods for the repair of a defective cardiac valve are provided. The implantable devices include an annuloplasty ring and a restraining and/or a remodeling structure or mechanism. The annuloplasty ring functions to reestablish the normal size and shape of the annulus bringing the leaflet in proximity to each other. A device having a remodeling structure further facilitates remodeling of the valve but allows the use of a flexible ring. The restraining structure functions to restrain the abnormal motion of at least a portion of the valve being repaired. The restraining and remodeling structures may include at least one strut across the interior of the circumference of the ring.

7 Claims, 21 Drawing Sheets

U.S. PATENT DOCUMENTS

| | | | |
|---|---|---|---|
| 6,793,673 B2 * | 9/2004 | Kowalsky et al. | 623/2.36 |
| 6,797,002 B2 | 9/2004 | Spence et al. | |
| 6,824,582 B2 * | 11/2004 | Wilson | 55/385.3 |
| 6,890,353 B2 | 5/2005 | Cohn et al. | |
| 6,908,478 B2 | 6/2005 | Alferness et al. | |
| 6,921,407 B2 * | 7/2005 | Nguyen et al. | 606/142 |
| 6,976,995 B2 | 12/2005 | Mathis et al. | |
| 6,997,950 B2 | 2/2006 | Chawla | |
| 7,070,618 B2 * | 7/2006 | Streeter | 623/2.36 |
| 7,125,421 B2 * | 10/2006 | Tremulis et al. | 623/2.37 |
| 7,144,363 B2 | 12/2006 | Pai et al. | |
| 7,166,126 B2 * | 1/2007 | Spence et al. | 623/2.36 |
| 7,166,127 B2 * | 1/2007 | Spence et al. | 623/2.37 |
| 7,247,134 B2 | 7/2007 | Vidlund et al. | |
| 7,311,729 B2 * | 12/2007 | Mathis et al. | 623/2.37 |
| 7,351,260 B2 | 4/2008 | Nieminen et al. | |
| 7,485,143 B2 * | 2/2009 | Webler et al. | 623/2.37 |
| 7,632,308 B2 | 12/2009 | Loulmet | |
| 7,828,842 B2 | 11/2010 | Nieminen et al. | |
| 2002/0173844 A1 | 11/2002 | Alfieri et al. | |
| 2003/0033009 A1 | 2/2003 | Gabbay | |
| 2003/0069593 A1 | 4/2003 | Tremulis et al. | |
| 2003/0093148 A1 | 5/2003 | Bolling et al. | |
| 2003/0120340 A1 | 6/2003 | Liska et al. | |
| 2003/0130731 A1 | 7/2003 | Vidlund et al. | |
| 2004/0127981 A1 | 7/2004 | Rahdert et al. | |
| 2004/0127982 A1 | 7/2004 | Machold et al. | |
| 2004/0138745 A1 | 7/2004 | Macoviak et al. | |
| 2005/0149182 A1 | 7/2005 | Alferness et al. | |
| 2006/0020336 A1 | 1/2006 | Liddicoat | |
| 2006/0247492 A1 * | 11/2006 | Streeter | 600/37 |
| 2007/0050020 A1 * | 3/2007 | Spence | 623/2.11 |
| 2008/0195126 A1 | 8/2008 | Solem | |
| 2010/0222876 A1 | 9/2010 | Hyde | |
| 2010/0298930 A1 | 11/2010 | Orlov | |

FOREIGN PATENT DOCUMENTS

| | | |
|---|---|---|
| WO | WO 91/02500 | 3/1991 |
| WO | WO 98/18411 | 5/1998 |
| WO | WO 99/13802 | 3/1999 |
| WO | WO 01/47438 | 7/2001 |
| WO | WO 01/89418 | 11/2001 |
| WO | WO-03028558 A2 * | 4/2003 |
| WO | WO 03/037227 | 5/2003 |
| WO | WO 2009/072114 | 6/2009 |

* cited by examiner

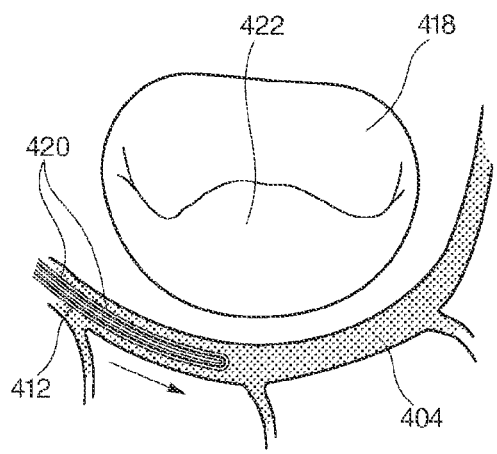
Fig. 20B
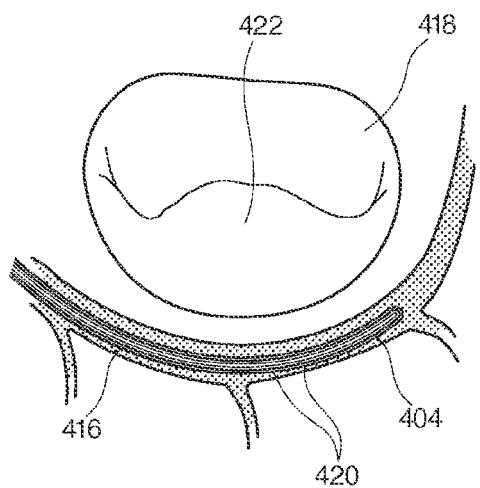
Fig. 20C
Fig. 20D
Fig. 20E
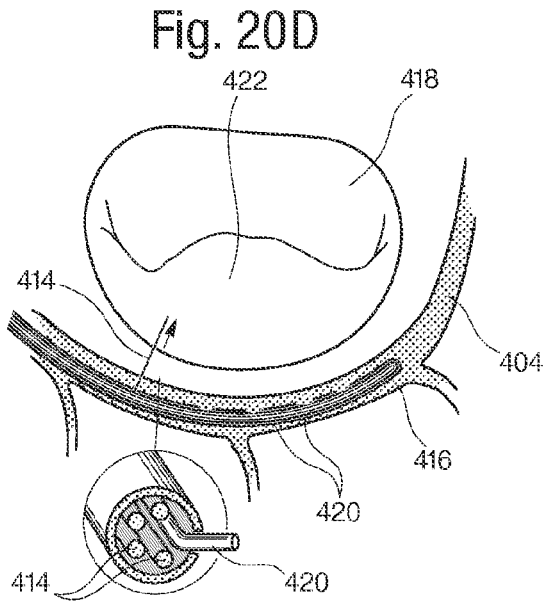
Fig. 20G
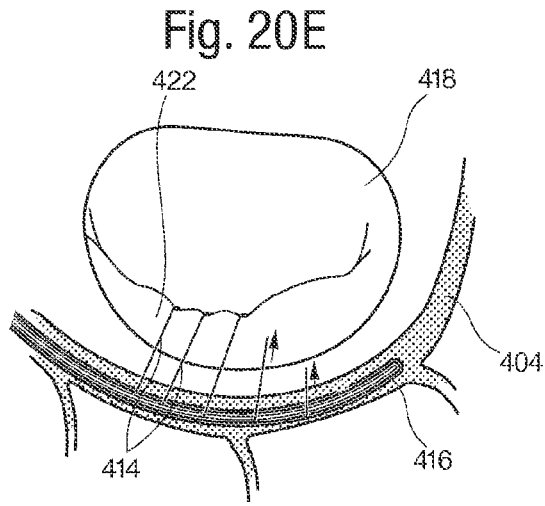

ANNULOPLASTY RINGS FOR REPAIRING CARDIAC VALVES

CROSS-REFERENCES RELATED TO APPLICATIONS

This is a continuation-in-part of U.S. patent application Ser. No. 10/613,761 filed on Jul. 2, 2003, now abandoned the disclosure of which is incorporated herein in its entirety.

FIELD OF THE INVENTION

The invention relates to devices and methods for facilitating and simplifying the repair of cardiac valves.

BACKGROUND OF THE INVENTION

The human heart has four valves which control the direction of blood flow in the circulation. The aortic and mitral valves are part of the "left" heart and control the flow of oxygen-rich blood from the lungs to the body, while the pulmonic and tricuspid valves are part of the "right" heart and control the flow of oxygen-depleted blood from the body to the lungs. The aortic and pulmonic valves lie between a pumping chamber (ventricle) and major artery, preventing blood from leaking back into the ventricle after it has been ejected into the circulation. The mitral and tricuspid valves lie between a receiving chamber (atrium) and a ventricle preventing blood from leaking back into the atrium during ejection.

Various disease processes can impair the proper functioning of one or more of these valves. These include degenerative processes (e.g., Barlow's Disease, fibroelastic deficiency), inflammatory processes (e.g., Rheumatic Heart Disease) and infectious processes (e.g., endocarditis). In addition, damage to the ventricle from prior heart attacks (i.e., myocardial infarction secondary to coronary artery disease) or other heart diseases (e.g., cardiomyopathy) can distort the valve's geometry causing it to dysfunction.

Heart valves can malfunction in one of two ways. Valve stenosis is present when the valve does not open completely causing a relative obstruction to blood flow. Valve regurgitation is present when the valve does not close completely causing blood to leak back into the prior chamber. Both of these conditions increase the workload on the heart and are very serious conditions. If left untreated, they can lead to debilitating symptoms including congestive heart failure, permanent heart damage and ultimately death. Dysfunction of the left-sided valves—the aortic and mitral valves—is typically more serious since the left ventricle is the primary pumping chamber of the heart.

Dysfunctional valves can either be repaired, with preservation of the patient's own valve, or replaced with some type of mechanical or biologic valve substitute. Since all valve prostheses have some disadvantages (e.g., need for lifelong treatment with blood thinners, risk of clot formation and limited durability), valve repair, when possible, is usually preferable to replacement of the valve. Many dysfunctional valves, however, are diseased beyond the point of repair. In addition, valve repair is usually more technically demanding and only a minority of heart surgeons are capable of performing complex valve repairs. The appropriate treatment depends on the specific valve involved, the specific disease/dysfunction and the experience of the surgeon.

The aortic valve is more prone to stenosis, which typically results from buildup of calcified material on the valve leaflets and usually requires aortic valve replacement. Regurgitant aortic valves can sometimes be repaired but usually also need to be replaced. The pulmonic valve has a structure and function similar to that of the aortic valve. Dysfunction of the pulmonic valve, however, is much less common and is nearly always associated with complex congenital heart defects. Pulmonic valve replacement is occasionally performed in adults with longstanding congenital heart disease.

Mitral valve regurgitation is more common than mitral stenosis. Although mitral stenosis, which usually results from inflammation and fusion of the valve leaflets, can often be repaired by peeling the leaflets apart (i.e., a commisurotomy), as with aortic stenosis, the valve is often heavily damaged and may require replacement. Mitral regurgitation, however, can nearly always be repaired but successful repair requires a thorough understanding of the anatomy and physiology of the valve, of the types of mitral valve dysfunction leading to mitral regurgitation and the specific diseases and lesions resulting in this dysfunction.

The normal mitral valve can be divided into three parts—an annulus, a pair of leaflets and a sub-valvular apparatus. The annulus is a dense ring of fibrous tissue which lies at the juncture between the left atrium and left ventricle. The annulus is normally elliptical or more precisely "kidney-shaped" with a vertical (anteroposterior) diameter approximately two-thirds of the horizontal diameter. The larger elliptical anterior leaflet and the smaller, crescent-shaped posterior leaflet attach to the annulus. Approximately two-thirds of the annulus is attached to the posterior leaflet and one-third to the anterior leaflet. The edge of the leaflet which is not attached to the annulus is known as the free margin. When the valve is closed, the free margins of the two leaflets come together within the valve orifice forming an arc in the shape of a "smile" known as the line of coaptation. The corners of this "smile", the two points on the annulus where the anterior and posterior leaflets meet (at approximately the 10 o'clock and 2 o'clock positions), are known as the commisures. The posterior leaflet is usually separated into three distinct scallops by small clefts which are referred to (from left to right) as P1, P2 and P3. The corresponding portions of the anterior leaflet directly opposite P1, P2 and P3 are referred to as A1, A2 and A3. The sub-valvular apparatus consists of two thumb-like muscular projections from the inner wall of the left ventricle known as papillary muscles and numerous chordae tendinae (or simply "chords") which are thin fibrous bundles which emanate from the tips of the papillary muscles and attach to the free margin or undersurface of the valve leaflets in a parachute-like configuration.

The normal mitral valve opens when the left ventricle relaxes (diastole) allowing blood from the left atrium to fill the decompressed left ventricle. When the left ventricle contracts (systole), the increase in pressure within the ventricle causes the valve to close, preventing blood from leaking into the left atrium and assuring that all of the blood leaving the left ventricle (the stroke volume) is ejected through the aortic valve into the aorta and to the body. Proper function of the valve is dependent on a complex interplay between the annulus, leaflets and subvalvular apparatus.

Lesions in any of these components can cause the valve to dysfunction, leading to mitral regurgitation. Physiologically, mitral regurgitation results in increased cardiac work since the energy consumed to pump some of the stroke volume of blood back into the left atrium is wasted. It also leads to increased pressures in the left atrium which results in back up of fluid in the lungs and shortness of breath—a condition known as congestive heart failure.

Mitral valve dysfunction leading to mitral regurgitation can be classified into three types based of the motion of the leaflets (known as "Carpentier's Functional Classification"). Type I dysfunction occurs despite normal leaflet motion. Lesions which can cause Type I dysfunction include a hole in the leaflet (usually from infection) or much more commonly distortion and dilatation of the annulus. Annular dilatation or distortion results in separation of the free margins of the two leaflets. This gap prevents the leaflets from coapting allowing blood to regurgitate back into the left atrium during systolic contraction.

Type II dysfunction results from leaflet prolapse. This occurs when a portion of the free margin of one or both leaflets is not properly supported by the subvalvular apparatus. During systolic contraction, the free margins of the involved portions of the leaflets prolapse above the plane of the annulus into the left atrium. This prevents leaflet coaptation and allows blood to regurgitate into the left atrium between the leaflets. The most common lesions resulting in leaflet prolapse and Type II dysfunction include chordal elongation or rupture due to degenerative changes (such as myxomatous pathology or "Barlow's Disease" and fibroelastic deficiency) or prior myocardial infarction.

Finally, Type III dysfunction results from restricted leaflet motion. Here, the free margins of portions of one or both leaflets are pulled below the plane of the annulus into the left ventricle. This prevents the leaflets from rising up to the plane of the annulus and coapting during systolic contraction. The restricted leaflet motion can be related to valvular or subvalvular pathology (usually fibrosis following damage from rheumatic heart disease)—referred to as Type IIIA dysfunction. It more commonly occurs when abnormal ventricular geometry or function leads to papillary muscle displacement which pulls the otherwise normal leaflets down into the ventricle, away from each preventing proper coaptation of the leaflets. This is known as Type IIIB dysfunction and usually results from prior myocardial infarction ("ischemia") or severe ventricular dilatation and dysfunction ("cardiomyopathy").

The anatomy and function of the tricuspid valve is similar to that of the mitral valve. It also has an annulus, chords and papillary muscles but has three leaflets (anterior, posterior and septal). The shape of the annulus is slightly different, more snail-shaped and slightly asymmetric. The demands on the tricuspid valve are significantly less than the mitral valve since the pressures in the right heart are normally only about 20% of the pressures in the left heart. Tricuspid stenosis is very rare in adults and usually results from very advanced rheumatic heart disease. Tricuspid regurgitation is much more common and can result from the same types of dysfunction (I, II, IIIA and IIIB) as the mitral valve. The vast majority of patients, however, have Type I dysfunction with annular dilatation preventing leaflet coaptation. This is usually secondary to left heart disease (valvular or ventricular) which can, over time, lead to increased pressures back stream in the pulmonary arteries, right ventricle and right atrium. The increased pressures in the right heart can lead to dilatation of the chambers and concomitant tricuspid annular dilatation.

The benefits of valve repair over replacement are now well established in the cardiac surgical literature in all types of valve dysfunction and in nearly all disease states. Patients undergoing valve repair have been shown to live longer, with better preservation of cardiac function. The vast majority of patients with mitral or tricuspid regurgitation can have their valves successfully repaired instead of replaced. The likelihood of a successful repair, however, is highly dependent on the skill, knowledge and experience of the individual surgeon. Although most surgeons are comfortable performing simple valve repairs (annuloplasty rings, limited leaflet resections, etc.), many rarely perform valve repairs and only a small minority of surgeons is facile at more complex valve repairs. Most surgeons have inadequate knowledge and training in these techniques and, even if they had the technical ability, they do not encounter enough patients to feel comfortable with complex cases. This variability in surgical skill is reflected in the wide range of valve repair rates among different centers. High-volume, experienced centers routinely report valve repair rates over 90% while the national average is only 20-30%.

A typical mitral valve repair involves various procedures or stages, each one correcting a specific abnormality of a specific component of the valve apparatus. Specific techniques are available for each component (annulus, leaflet segments, chords, and papillary muscles) of the valve. The annular circumference and shape can be restored with an annuloplasty device (ring or band) which is attached to the annulus using sutures. Annular calcification can be excised. Excess or prolapsing leaflet tissue can be resected and reconstructed. Shrunken or restricted leaflet segments can be augmented with a patch of autologous tissue. Leaflet segments can be partially detached from the annulus and advanced to cover a gap from a leaflet resection (known as a sliding valvuloplasty). Ruptured or elongated chords can be replaced with artificial chords or by transferring redundant chords from another leaflet segment. Shrunken or fused chords can be released or split. Occasionally, the papillary muscles themselves can be shortened to correct prolapse from multiple elongated chords.

The power of Carpentier's functional classification system is that the appropriate surgical techniques derive directly from the type of dysfunction. Patients with Type I valve dysfunction (normal leaflet motion due to annular dilatation) and Type IIIB valve dysfunction (restricted leaflet motion due to ventricular distortion) can usually be repaired with implantation of an annuloplasty ring alone. In Type I valve dysfunction, the annuloplasty is sized based on the dimensions of the anterior leaflet to restore the annulus to its original size. In Type IIIB valve dysfunction, the annuloplasty must be downsized to account for restricted leaflet motion.

Patients with Type II and IIIA valve dysfunction usually require more complex repairs. Type IIIA valve dysfunction (restricted leaflet motion due to valvular/subvalvular pathology) can require leaflet augmentation and/or chordal release/ splitting. Type II valve dysfunction (leaflet prolapse) usually requires some type of leaflet resection and reconstruction along with, on occasion, additional leaflet and chordal procedures. The most common type of valve repair for Type II valve dysfunction is a quadrangular resection of the middle (P2) segment of the posterior leaflet with advancement and approximation of the remaining (P1 and P3) segments (a sliding valvuloplasty). Many surgeons are comfortable repairing straightforward cases of P2 prolapse. More complex Type II cases, including those with anterior leaflet involvement or prolapse at or near the commisures, usually require additional procedures such as chordal transfer, placement of artificial chords or additional leaflet resections. Most surgeons, outside of specialized centers, rarely tackle these complex repairs and these patients usually receive a valve replacement. New devices or techniques which simplify complex Type II repairs would greatly expand the proportion of patients who benefit from valve repair over replacement.

Nearly all experienced valve repair surgeons agree that all patients undergoing mitral valve repair must have an annuloplasty procedure performed to assure a successful, durable repair. The annuloplasty serves two main purposes. It restores the shape and size of the annulus to permit adequate leaflet coaptation and prevent regurgitation. It also serves to stabilize any additional repair work by taking tension off of any suture lines. Although annuloplasties were originally performed using a suture woven in and out of the annulus like a purse string, nearly all surgeons today utilize a prosthetic annuloplasty device. This is usually a prosthetic ring or band that is attached within the heart to the dilated and distorted annulus using multiple sutures. The annuloplasty usually includes an inner frame made of metal, such as stainless steel or titanium, or of a flexible material, such as silicone rubber or Dacron cordage, and is covered with a biocompatible fabric or cloth into which the sutures are placed. The rings may be rigid, semi-rigid or flexible, and they may form a complete continuous ring, a split ring or a partial ring or band. Annuloplasty rings may be provided in one of several shapes—circular, D- or "kidney" shaped or C-shaped. Rings are usually specifically designed for the mitral or tricuspid valves. An annuloplasty ring system usually consists of rings of various sizes (24 to 40 mm) loaded on specialized holders to facilitate placement along with a series of sizers to measure the dimensions of the patient's valve.

Common examples of rigid annuloplasty rings are the original Carpentier ring disclosed in U.S. Pat. No. 3,656,185, the more current Carpentier-Edwards® ring (distributed by Edwards Laboratories) disclosed in U.S. Pat. No. 5,061,277, and the ring disclosed in U.S. Pat. No. 4,164,046, which are hereby incorporated by reference. Examples of semi-rigid annuloplasty rings include the Carpentier-Edwards Physio™ ring as disclosed in U.S. Pat. No. 5,104,407 and the ring disclosed in U.S. Pat. No. 4,489,446, which are hereby incorporated by reference. Common examples of flexible rings include the Duran ring (distributed by Medtronic) as disclosed in Duran et al., Circulation (Suppl. I) 78:91-96(1989) and the Puig-Massana ring as disclosed in U.S. Pat. No. 4,290,151, which are hereby incorporated by reference. Other annuloplasty rings include the Seguin Ring (made by St. Jude), the Carbomedics rings, the Colvin-Galloway Ring (made by Medtronic), the Carpentier Tricuspid Ring and the Edwards MC3 Tricuspid Ring.

Each of these types of annuloplasty rings has advantages and disadvantages that are commonly understood in the field of mitral valve repair. Rigid and semi-rigid rings are believed to more completely restore the shape as well as the circumference of the annulus. As such they are said to perform a "remodeling" (shape restoring) annuloplasty in addition to a "reduction" (circumference decreasing) annuloplasty. It has been shown experimentally that restoring and fixing the vertical (anteroposterior) dimension of the annulus is critical to restoring leaflet coaptation and thus to a successful annuloplasty procedure. Rigid and semi-rigid rings more reliably fix this dimension than flexible rings. Flexible rings, however, are somewhat easier to insert and secure to the annulus which might decrease the (albeit low) incidence of post-operative ring detachment ("dehiscence"). They are also purported to preserve the normal three dimensional "saddle" shape of the annulus and its complex motion during the cardiac cycle. Complete rings (rigid or flexible) have the advantage of fixating the entire annulus which should decrease the incidence of late failures due to progressive dilatation of the annulus. Partial rings (more precisely bands) are designed to reduce and fixate the posterior annulus only and are based on the fact that the anterior third of the annulus is part of the fibrous skeleton of the heart and should be less prone to dilate. The advantage of a partial band is that it requires less sutures to secure and eliminates the anterior annular sutures which are typically the most difficult to visualize and place.

Since they involve work inside the heart chambers, conventional procedures for replacing or repairing cardiac valves require the use of the heart-lung machine (cardiopulmonary bypass) and stopping the heart by clamping the ascending aorta and perfusing it with high-potassium solution (cardioplegic arrest). Although most patients tolerate limited periods of cardiopulmonary bypass and cardiac arrest well, these maneuvers are known to adversely affect all organ systems. The most common complications of cardiopulmonary bypass and cardiac arrest are stroke, myocardial "stunning" or damage, respiratory failure, kidney failure, bleeding and generalized inflammation. If severe, these complications can lead to permanent disability or death. The risk of these complications is directly related to the amount of time the patient is on the heart-lung machine ("pump time") and the amount of time the heart is stopped ("crossclamp time"). Although the safe windows for pump time and cross clamp time depend on individual patient characteristics (age, cardiac reserve, comorbid conditions, etc.), pump times over 4 hours and clamp times over 3 hours can be concerning even in young, relatively healthy patients. Complex valve repairs can push these time limits even in the most experienced hands. Even if he or she is fairly well versed in the principles of mitral valve repair, a less experienced surgeon is often reluctant to spend 3 hours trying to repair a valve since, if the repair is unsuccessful, he or she will have to spend up to an additional hour replacing the valve. Thus, time is a major factor in deterring surgeons from offering the benefits of valve repair over replacement to more patients. Devices and techniques which simplify and expedite valve repair would go a long way to eliminating this deterrent.

Within recent years, there has been a movement to perform many cardiac surgical procedures "minimally invasively" using smaller incisions and innovative cardiopulmonary bypass protocols. The purported benefits of these approaches include less pain, less trauma and more rapid recovery. This has included "off-pump coronary artery bypass" (OPCAB) surgery which is performed on a beating heart with the use of cardiopulmonary bypass and "minimally invasive direct coronary artery bypass" (MIDCAB) which is performed through a small thoracotomy incision. A variety of minimally invasive valve repair procedures have been developed whereby the procedure is performed through a small incision with or without videoscopic assistance and, more recently, robotic assistance. However the use of these minimally invasive procedures has been limited to a handful of surgeons at specialized centers. Even in their hands, the most complex valve repairs cannot be performed since dexterity is limited and the whole procedure moves more slowly. Devices and techniques which simplify valve repair have the potential to greatly increase the use of minimally invasive techniques which would significantly benefit patients.

Thus, it is desirable to provide a single device which, when operatively used, only requires a simplified procedure by which to repair a cardiac valve, and a mitral valve in particular. For example, it would be beneficial to provide a device which, when properly implanted, not only remodels the defective valve annulus but also corrects other problems, such as leaflet prolapse, thereby obviating the need to perform ancillary procedures to correct leaflet size and shape, to reattach or shorten chordae, etc. With such a device, most patients with Type II valve dysfunction could be corrected by device implantation alone or with a limited P2 leaflet resection. Many patients with Type IIIA valve dysfunction could be corrected with aggressive leaflet mobilization (chordal cutting) followed by device implantation. Simplifying the repair procedure would decrease the amount of time the patient's heart would need to be stopped and bypassed with a heart-lung machine and increase the likelihood that it could be performed minimally invasively. This would not only decrease the potential for complications, it would also allow a broader group of surgeons to perform the procedure.

RELEVANT LITERATURE

1. Mohty D, Orszulak T A, Schaff H V, Avierinos J F, Tajik J A, Enriquez-Sarano M. Very Long-Term Survival and Durability of Mitral Valve. Circulation 2001; 104[suppl I]: I-1-I-7.
2. Chauvaud, S.; Fuzellier, J. F.; Berrebi, A.; Deloche, A.; Fabiani, J. N., and Carpentier, A. Long-term (29 years) results of reconstructive surgery in rheumatic mitral valve insufficiency. Circulation 2001; 104(12 Suppl 1):I12-5.
3. Braunberger, E.; Deloche, A.; Berrebi, A.; Abdallah, F.; Celestin, J. A.; Meimoun, P.; Chatellier, G.; Chauvaud, S.; Fabiani, J. N., and Carpentier, A. Very long-term results (more than 20 years) of valve repair with Carpentier's techniques in nonrheumatic mitral valve insufficiency. Circulation. 2001; 104(12 Suppl 1):I8-11.
4. Carpentier, A. F.; Lessana, A.; Relland, J. Y.; Belli, E.; Mihaileanu, S.; Berrebi, A. J.; Palsky, E., and Loulmet, D. F. The "physio-ring": an advanced concept in mitral valve annuloplasty. Ann Thorac Surg. November 1995; 60(5): 1177-85.
5. Carpentier, A. Cardiac valve surgery—the "French correction". J Thorac Cardiovasc Surg. September 1983; 86(3): 323-37.
6. Aklog, L.; Adams, D. H.; Couper, G. S.; Gobezie, R.; Sears, S., and Cohn, L. H. Techniques and results of direct-access minimally invasive mitral valve surgery: a paradigm for the future. J Thorac Cardiovasc Surg. November 1998; 116(5): 705-15.
7. Savage E B, Ferguson T B, DiSesa V J. Use of Mitral Valve Repair: Analysis of Contemporary United States Experience Reported to the Society of Thoracic Surgeons National Cardiac Database. Ann Thorac Surg 2003; 75:820-5.

SUMMARY OF THE INVENTION

The present invention includes annuloplasty devices and methods of using the subject devices to repair cardiac valves. Kits including at least one of the subject devices are also provided.

The present invention is particularly suitable for repairing regurgitant mitral valves. Certain variations of the present invention are directed to correcting the shape and size of the valve's annulus to fully correct mitral regurgitation when leaflet motion is normal (Type I valve dysfunction). Other variations are directed to correcting regurgitant valves secondary to Type II valve dysfunction (leaflet prolapse). Still yet, other variations are directed to treating more than one type of dysfunction, such as both Type I and Type II dysfunctions. Additionally, variations of the present invention may address and correct leaflet billowing which occurs as a result of or subsequently to repairing a regurgitant valve. Accordingly, it should be understood that, while the present invention is described in the context of exemplary valve repair applications, the present invention has potential for use in correcting all types of mitral or tricuspid valve dysfunction.

An object of the present invention is to simplify the mitral valve repair procedures and obviate the need to perform anything other than an annuloplasty procedure, i.e., implantation of the annuloplasty ring, to completely correct a defective cardiac valve regardless of the number and types of particular defects inflicting the valve. Another object of the invention is to employ a single device and a single-procedure to completely correct valve dysfunction. In certain circumstances where the device might not completely eliminate the need for adjunctive procedures, the number and complexity of these procedures and the time and expertise necessary to perform them would be significantly reduced.

As is known from the use of conventional annuloplasty rings, even a properly sized and implanted ring, while adequately correcting the shape and size of the valve's annulus to fully correct mitral regurgitation when leaflet motion is normal (Type I valve dysfunction), does not necessarily bring the valve to full proper functioning when leaflet prolapse (Type II valve dysfunction) or severe leaflet restriction (Type III valve dysfunction) is present. Ancillary procedures, including leaflet resection, chordal transfer and reattachment are usually required for leaflet prolapse and leaflet augmentation or chordal resection may be required for restricted leaflet motion.

A feature of the present invention is the provision of an implantable device having an annuloplasty ring and one or more structures extending within the ring. The annuloplasty ring functions remodel the valve, i.e., to correct the shape and size of the annulus, thereby bringing the leaflets in proximity to permit coaptation. The particular function of the structure(s) is dependent upon the configuration, physical characteristics and relative positioning of the structure(s). In certain embodiments, the structures act to restrain the abnormal motion of at least a portion of one or more of the valve leaflets. In other embodiments, the structures facilitate customized remodeling of the annulus. In certain other embodiments, the structures provide a remodeling as well as a leaflet restraint function where the latter may address latent or residual billowing of the leaflet body and/or latent or residual prolapsing of the leaflet edge, either of which may result from the remodeling itself or from a physiological defect.

The ring portion of the subject devices may have a complete or partial configuration, may be rigid, semi-rigid or flexible, and may any suitable three-dimensional shape to address the particular application at hand. The interior structures include of one or more members, crossbars or struts extending inside the orifice of the ring. The members may have a variety of different shapes and configurations including, but not limited to, chord-shaped or ribbon-shaped, or may be rigid, semi-rigid or flexible, straight or bowed, elastic or inelastic or solid. They can attach to the ring or to another member, forming any pattern suitable to address the various defects of the valve. By restraining the prolapsing or billowing leaflet segment and/or by providing a new intra-annular coaptation plane, the subject devices facilitate coaptation of the leaflets(s) thereby eliminating the regurgitation.

Thus, the subject devices function to ensure proper coaptation of the leaflets, regardless of the number, type and anatomical location of the valvular defects, without the need for procedures other than proper implantation of the ring in most cases. As a result, specific chordal or leaflet procedures may not need to be performed as their collective ill effects can be resolved solely by implantation of the subject device. In some cases, the surgeon may choose to perform relatively straight-forward ancillary procedures such as a limited posterior leaflet resection or mobilization while allowing the restraint mechanism to correct any new or residual prolapse.

The methods of the present invention are directed to repairing a defective cardiac valve. In one method, the defective cardiac valve accessed and a subject device, such as those described above, is implanted adjacent the defective cardiac valve wherein the abnormal function of the valve is corrected. The correction may be accomplished by restraining a prolapsing segment of the leaflet during systole and/or by remodeling the valve annulus.

In certain methods the ring portion of the device is attached to the valve annulus, while in others, the ring portion of the device is positioned within the coronary sinus.

BRIEF DESCRIPTION OF THE DRAWINGS

FIG. 6B has intersecting restraints extending between a primary restraint and the posterior segment of the ring.

DETAILED DESCRIPTION OF THE INVENTION

Figure 1A:
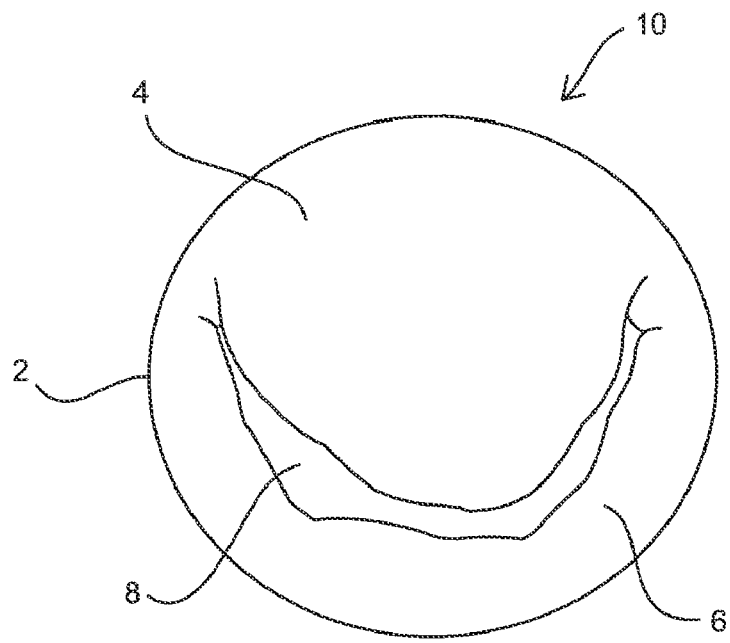
FIG. 1A is a top view of a mitral valve having a dilated and deformed annulus (circular rather than elliptical) resulting in poor coaptation of the anterior and posterior leaflets with a visible gap between therebetween.

The present invention includes implantable prosthetic devices and methods of using the subject devices to repair cardiac valves. The prosthetic devices include annuloplasty rings which, when operatively employed, are sutured into the annulus of a defective or deformed valve, thereby correcting the defect or deformation and rendering the valve competent.

Kits including at least one of the subject devices are also provided. The present invention is particularly suitable for repairing the mitral valve and, thus, is described in the context of mitral valve repair for purposes of example only. However, the present invention is also suitable for the repair of tricuspid valves and other valves.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The terms "annuloplasty ring" and "ring" are used interchangeably herein when referring to the annular member of the annuloplasty devices of the present invention and are meant to encompass any configuration or shape of annuloplasty ring including, but not limited to, configurations which are partial or split (i.e., have an open circumference) or continuous (i.e., have a closed circumference), including, but not limited to, flexible, semi-rigid and rigid devices and including, but not limited to, shapes which are circular, D-shaped, C-shaped, saddle shaped and any other annular or non-annular shape suitable for repairing cardiac valves, whether or not specifically described herein.

The term "annuloplasty device" as used herein includes the annuloplasty ring of the present invention in addition to any and all other components, e.g., the restraining structure, integral with the ring.

The terms "major axis" and "longitudinal axis" are used interchangeably herein when referring to the axis defined generally along the direction of a greater diameter of those annuloplasty rings of the present invention having other than a circular shape.

The terms "minor axis" and "transverse axis" are used interchangeably herein when referring to the axis defined generally along the direction transverse to the major axis of those annuloplasty rings of the present invention having other than a circular shape.

The term "horizontal axis" is used herein when referring to the axis which bisects, generally in the horizontal direction according to the views depicted in the relevant Figures herein, those annuloplasty rings of the present invention having a circular shape.

The term "vertical axis" is used herein when referring to the axis which bisects, generally in the vertical direction according to the views depicted in the relevant Figures herein, those annuloplasty rings of the present invention having a circular shape.

Figure 1B:
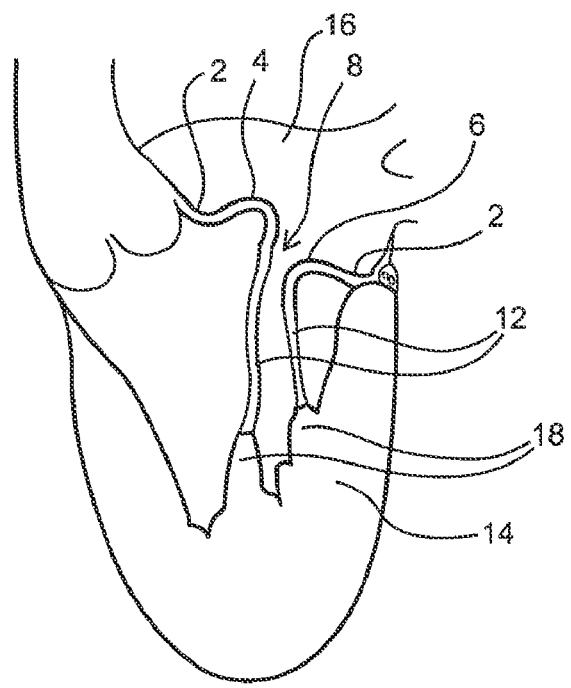
FIG. 1B is a cross-sectional view of the left side of the heart illustrating the left atrium, the left ventricle, the dysfunctional mitral valve of FIG. 1A, the aortic valve and the ascending aorta. The anterior leaflet of the mitral valve is shown prolapsing into the left atrium above the plane of the annulus as a result of an elongated chord. This prevents it from coapting against the posterior leaflet thereby creating a gap which results in regurgitation of blood into the left atrium during systolic contraction.

Referring now to the drawings, wherein like reference numbers refer to like components throughout the drawings, FIG. 1A illustrates a top view, i.e., 10 as viewed from the left atrium, of a regurgitant mitral valve having an annulus 2, anterior leaflet 4 and posterior leaflet 6. Mitral valve 10 suffers from poor coaptation of the leaflets as evidenced by gap 8 between them. In addition, the annulus 2 is dilated and deformed, taking on a circular instead of a kidney shape. FIG. 1B is a cross-sectional view of the left side of a heart having a left ventricle 14, a left atrium 16 and mitral valve 10 situated at the atrioventricular passageway there between. The anterior leaflet 4 and posterior leaflet 6 are connected to the papillary muscles 18 by chordae tendinae 12. Mitral valve 10 has Type II valve dysfunction with prolapse of the free margin of the anterior leaflet 4 above the plane of the annulus 2 as a result of elongation of the chordae 12 to this leaflet. This prolapse prevents the anterior leaflet 4 from coapting with posterior leaflet 6 resulting in a gap 8 through which blood regurgitates from the left ventricle 14 into the left atrium 16 during systolic contraction. FIG. 1B further illustrates the effect that the dilation of the annulus 10 has on incomplete coaptation. The various embodiments of the annuloplasty devices of the present invention, which will now be described in detail, function to correct the defective mitral valve 10 when properly implanted therein.

Figure 2A:
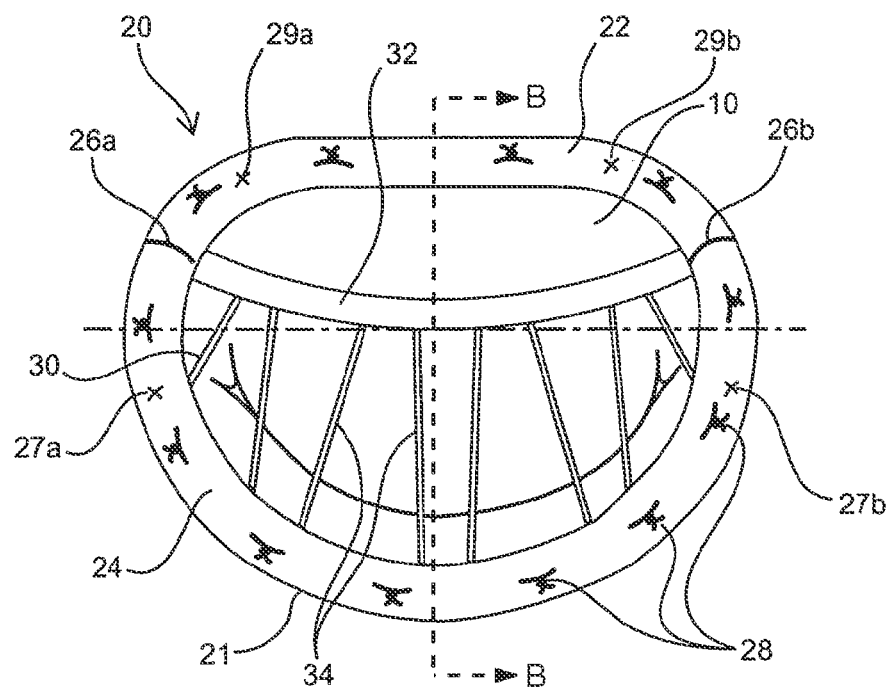
FIG. 2A is a view from the left atrium of one embodiment of a D-shaped annuloplasty device of the present invention, shown operatively attached to the annulus of the mitral valve of FIG. 1A, having a restraining structure including a primary, horizontal restraint and secondary restraints crossing between it and the posterior portion of the device body across the line of coaptation of the valve leaflets.

FIGS. 2A and B illustrate one embodiment of an annuloplasty device 20 of the present invention. Device 20 includes a complete D-Shaped semi-rigid ring 21 operatively implanted into the defective mitral valve 10 by means of a plurality of interrupted mattress sutures 28 which are sewn through ring 21 and into the annulus (not visible due to obstruction by ring 21). Other means known in the art for attaching annuloplasty rings may also be used with those of the present invention including, but not limited to, a continuous running suture, interrupted simple (non-mattress) sutures, specialized clips or staples. The commissural marks 26a and 26b are guides to identify the approximate location of the valve commissures and separate the ring into an anterior segment 22 and posterior segment 24.

Extending across a portion of the interior area of the ring 21 is a net-like restraining structure 30. Restraining structure 30 can include any number of restraining members, crossbars or struts in any pattern as long as they create a net which covers any prolapsing segments of either leaflet. The number of restraining members, the gaps between them and their pattern can be optimized to maximize the ability of the restraining structure to restrain prolapsing tissue, while minimizing the amount of prosthetic material in contact with leaflet tissue and avoiding any turbulence and obstruction to flow. In this particular embodiment, a primary crossbar restraint 32 extends across the major axis of ring 21. More specifically, cross-restraint 32 spans ring 21 between commissural junctures 26a and 26b; however, cross restraint 32 may extend between and attach to ring 21 at any appropriately corresponding locations on either side of junctures 26a and 26b. For example, cross restraint 32 may extend between corresponding locations 27a and 27b, or between corresponding locations 29a and 29b. Secondary restraining members 34 extend generally along the minor axis from the posterior ring segment 24 over the line of coaptation 8 to the primary crossbar restraint 32.

Figure 2B:
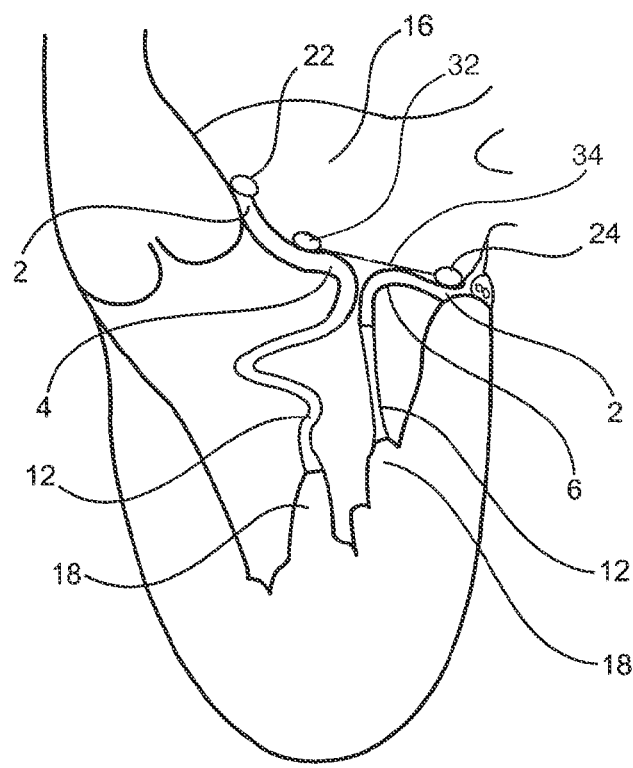
FIG. 2B is a cross-sectional view of the left side of the heart having the annuloplasty device of FIG. 2A operatively implanted (shown along line b-b) within and correcting the defective mitral valve within the heart of FIG. 1B. The restraining structure corrects the defective mitral valve by preventing the anterior leaflet of the valve from prolapsing into the left atrium above the plane of the annulus, allowing it to coapt against the posterior leaflet of the valve.

As can be seen in FIGS. 2A and 2B, when operatively implanted into the regurgitant mitral valve 10, anterior segment 22 of ring 21 is attached to the anterior portion of mitral valve annulus 2, which abuts and is supported by the base of aorta 25. Posterior segment 24 of ring 21 is attached to the posterior portion of annulus 2. As such, annuloplasty ring 21 functions to remodel valve annulus 2 to its proper shape and size, thereby bringing leaflets 4 and 6 into proximity. In patients with Type I valve dysfunction (pure annular dilatation with normal leaflet motion) this annular remodeling and re-approximation of the two leaflets 4 and 6 would suffice to permit adequate coaptation of the leaflets. In patients with Type II valve dysfunction (leaflet prolapse), one or more leaflet segments are not supported by the subvalvular apparatus as a result of chordal elongation or rupture. In the illustrated example (FIG. 1B), the anterior leaflet 4 prolapses into the left atrium as a result of elongation of the chordae 12. Thus, bringing the leaflets in proximity to each other is not adequate to assure proper leaflet coaptation since the prolapsing anterior leaflet 4 is displaced into the left atrium 16 during systolic contraction maintaining the gap 8 through which blood can still regurgitate. Conventional valve repair would require adjunctive procedures to the prolapsing anterior leaflet 4 or the elongated chord 12 to correct the prolapse. With insertion of the annuloplasty device 20, however, the restraining structure 30 prevents the prolapsing anterior leaflet 4 from being displaced into the left atrium. By keeping this segment under the plane of the annulus 2, the restraining structure 30 allows the previously prolapsing anterior leaflet 4 to coapt against the non-prolapsing posterior leaflet 6 which has been brought into proximity to anterior leaflet 4 by the remodeling effect of the annuloplasty ring 21.

To understand the ability of the restraining structure 30 to correct regurgitation resulting from Type II valve dysfunction and various design considerations for the structure 30, it is important to emphasize the precise definition of leaflet prolapse and contrast it to leaflet billowing. With leaflet prolapse the free margin or edge of the leaflet (where the chordae are attached) is displaced into the left atrium 16 during systolic contraction preventing leaflet coaptation and results in regurgitation. With leaflet billowing, on the other hand, the body of the leaflet balloons into the left atrium above the plane of the annulus but the free margin remains below the plane of the annulus. The coapting portion of the leaflet near the free margin remains below the plane of the annulus; it is able to coapt with the other leaflet as long as they are in proximity and not separated as a result of annular dilatation. Leaflet billowing is abnormal, may result in increased stress on the attached chordae and is thought to be a precursor to prolapse and regurgitation. It may also contribute to late failures after mitral valve repair as a result of increased chordal stress. Leaflet billowing, however, does not cause mitral regurgitation unless it is associated with leaflet prolapse.

In order to correct leaflet prolapse, the net-like restraining structure 30, at a minimum, preferably covers the entire posterior leaflet 6, the gap 8 between the leaflets and the coapting portion of the anterior leaflet 4 (the portion which would normally make contact with the posterior leaflet 4) such as that illustrated in FIG. 2A. As such, cross-restraint 32 is positioned at least a requisite distance from posterior segment 24 of ring 21. Exemplary end-to-end fixation locations for cross-restraint 32 are identified on ring 21 at 26a and 26b or, alternatively, at 27a and 27b or at 29a and 29b. The greater this distance, the greater the length of the restraining members 34. While sufficient coverage of the posterior leaflet 6 is necessary, the increased length in the restraining members increases the amount of prosthetic material in contact with the leaflet tissue which may result in increased turbulence and obstruction of blood flow. Thus, a primary advantage of minimizing the surface area of the net-like restraining structure 30 is decreasing the amount of prosthetic material in contact with leaflet tissue and thereby decreasing the amount of turbulence and obstruction to blood flow. However, there may be several potential disadvantages with such a minimal configuration. First, if the posterior leaflet is large and an adjunctive posterior leaflet resection is not performed, the line of coaptation 8 could lie significantly more anterior than is shown in FIG. 2A. If this occurred the net-like restraining structure might not fully cover the line of coaptation 8 which would allow a prolapsing segment of the anterior leaflet 4 to protrude through the device and cause regurgitation. A similar situation may occur where there is significant billowing of the anterior leaflet 4. If the billowing segment protrudes anterior to the cross restraint (i.e., outside of the net), it could, if severe, drag a prolapsing segment with it preventing coaptation and causing regurgitation. Finally, even if billowing of the anterior leaflet does not result in prolapse, it could nonetheless put additional stress on the chords which might impact the long-term durability of the repaired valve. Therefore, it might be desirable to restrain the billowing portion as well as the prolapsing portion of the anterior leaflet which might require a larger restraining structure 30 with the cross-restraint positioned closer to the anterior annulus 22 or, perhaps, extending the restraining members across the entire diameter of the ring (eliminating the need for a cross-restraint), such as provided in the embodiments of FIGS. 3C and 3D.

The design considerations for the secondary restraining members 34 are similar. The number of restraint members 34 is preferably kept to a minimum to minimize the amount of prosthetic material and the consequences thereof. The force generated by the prolapsing leaflet segment as it abuts the restraining structure 30 will be distributed across the restraint member with which it is in contact. Therefore, increasing the number of restraining members would decrease the stress on each individual member allowing it to be constructed from a finer gauge material. However, if there are too few restraining members, the gap between them might be wide enough to allow a prolapsing segment of either leaflet to slip through the gap unrestrained. The standard teaching in mitral valve repair is that the free margin of a leaflet must be supported by a good quality chord 12 (i.e., one that is not elongated or too thin) at least every 5-7 millimeters along the leaflet. Using this guideline, device 20 should have secondary restraint members 34 spaced at a similar interval or slightly wider. It is also possible that the optimal configuration would have these members spaced unevenly to accommodate greater prolapsing forces centrally than near the commissures.

FIGS. 3A-D illustrate a few other exemplary embodiments of a D-shaped annuloplasty device of the present invention, each including a ring 52 having anterior segment 54 and posterior segment 56 with their respective circumferential lengths are determined by the location of junctures 64a, 64b. Device 50 of FIG. 3A has restraining structure 58 which has a configuration generally similar to that of restraining structure 30 of annuloplasty device 20 of FIG. 2A, and defined by primary cross-restraint 60 and secondary restraints 62. Primary cross-restraint 60 has a configuration and is positioned similar to that of cross-restraint 32 of FIG. 2A; however, secondary restraints 62, of which there are twelve, have a running zigzag pattern between cross-restraint 60 and posterior segment 56. Also, the thickness of cross-restraint 60 is substantially greater than that of secondary restraints 62.

Figure 3A:
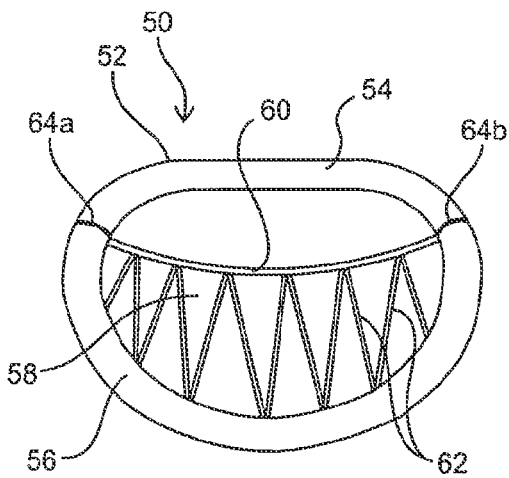
FIGS. 3A-D illustrate four other exemplary embodiments of the annuloplasty device of the present invention having a D-shaped configuration, wherein the device of FIG. 3A has zigzagging secondary restraints extending between a primary horizontal restraint and the posterior segment of the ring; the device of FIG. 3B has intersecting secondary restraints extending between a primary, horizontal restraint and the posterior segment of the ring; the device of FIG. 3C has intersecting restraints extending between the anterior and posterior segments of the ring without a primary restraint; and the device of FIG. 3D has parallel restraints extending between the anterior and posterior segments of the ring without a primary restraint.
Figure 3B:
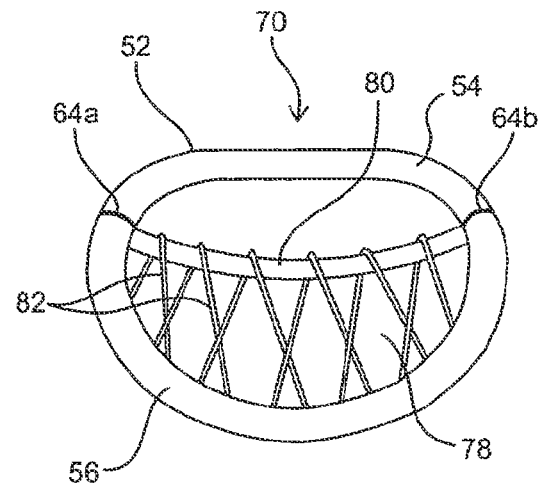

Annuloplasty device 70 of FIG. 3B has cross-restraint 80 having a configuration the same as annuloplasty device 50 of FIG. 3A; however, secondary restraints 82 have a criss-crossing pattern or form a series of "Xs". Each leg or secondary restraint 82 of each X may extend between and have its ends attached to cross-restraint 80 and posterior segment 56 of ring 52. Alternatively, as illustrated in FIG. 4B, the criss-crossing pattern may be formed by a plurality of restraint members, each wrapped a single time around cross-restraint 80 and having their respective ends affixed to posterior segment 56. The attachment points of the respective strands are staggered such that the resulting criss-crossing pattern of restraining structure 78 is formed. Similar to the device of FIG. 2A, primary cross-restraint 80 is thicker than secondary restraints 82.

Figure 3C:
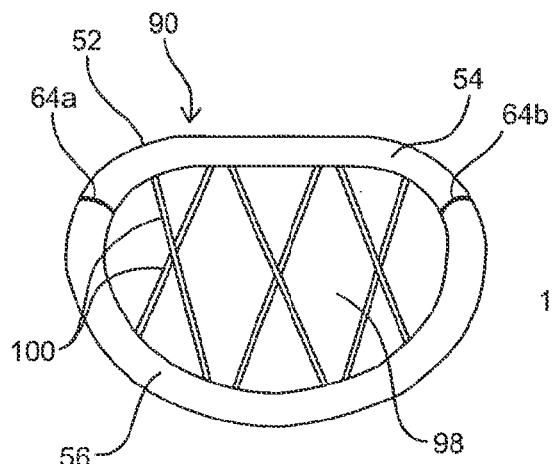
Figure 3D:
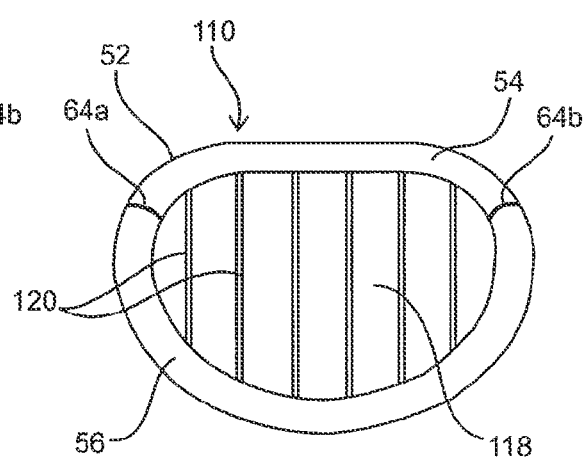

FIGS. 3C and 3D illustrate annuloplasty devices 90 and 110 with restraining structures 98 and 118 which, unlike the previously described annuloplasty devices of the present invention, do not include a cross-restraint member and thus covers the entire ring orifice with transverse restraints extending from the anterior segment 54 to the posterior segment 56 of the ring. In FIG. 3C, the transverse restraining members 100 are substantially transverse to the major axis of ring 52 and are configured in a criss-crossing pattern wherein each of the legs of the Xs is attached to ring 52. FIG. 3D illustrates another D-shaped annuloplasty device 110 having a restraining structure 118 having only transverse restraints 120. Transverse restraints 120 are parallel to each other and extend between and are attached to anterior segment 54 and posterior segment 56 of ring 52.

FIGS. 4A-D illustrate annuloplasty devices having a circular ring 124 configuration. Circular rings tend to be completely flexible and reduce the circumference of the annulus without remodeling it to a specific shape. Surgeons who use circular rings value the precise, measured reduction of the annular circumference but feel that ring flexibility is important to maintain the normal dynamic geometry of the annulus and to minimize the risk of ring dehiscence (late detachment secondary to poor healing of the ring to the annulus). Each of the rings 124 have an anterior segment 126 and a posterior segment 128 attached to each other at junctures 130a, 130b. Anterior segment 126 extends over approximately ⅓ of ring 124 and the remaining approximate ⅔ of ring 124 comprise posterior segment 128. The restraining structures of each of these annuloplasty devices 122 have varying configurations that will now be discussed individually.

Figure 4A:
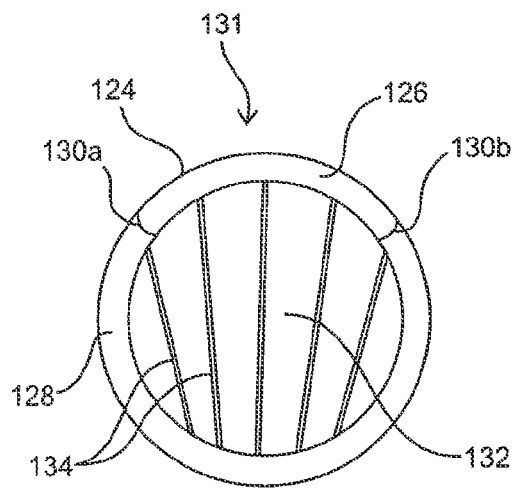
FIGS. 4A-D illustrate four exemplary embodiments of the annuloplasty devices of the present invention having a circular ring, wherein the device of FIG. 4A has substantially parallel transverse restraints extending between the anterior and posterior segments of the ring; the device of FIG. 4B has zigzagging restraints extending between the anterior and posterior segments of the ring; the device of FIG. 4C has substantially parallel or slightly angular secondary restraints extending between a primary cross-restraint and the posterior segment of the ring; and the device of FIG. 4D has a smaller, inner ring substantially concentric within the outer annuloplasty ring and intersecting restraints extending between the inner and outer rings.
Figure 4B:
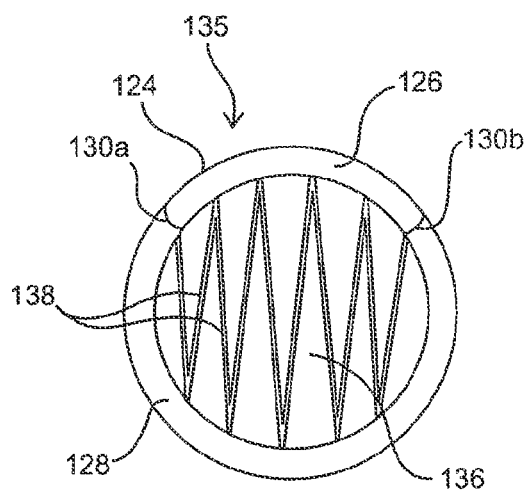

The restraining structure 132 of annuloplasty device 131 of FIG. 4A includes five (but may include more or less) varying-length restraints 134 along the vertical axis, wherein the three central restraints 134 extend between anterior segment 126 and posterior segment 128 of ring 124, and the two outer restraints each extend between respective points on posterior segment 128 only. As with all embodiments of the present invention, any suitable number and ring attachment locations of restraints 134 may be employed. Restraints 134 do not intersect each other within the interior of ring 124 and are not quite parallel to each other. Instead, restraints 134 extend somewhat radially from the center section of posterior segment 128 to either the anterior segment 126 or the distal portion of posterior segments 128.

The restraining structure 136 of annuloplasty device 135 of FIG. 4B also provides restraints 138 which extend between sides of ring 124 generally along the vertical axis but in a zigzag configuration. Here, ten restraints 138 are employed, but more or less may be used.

Figure 4C:
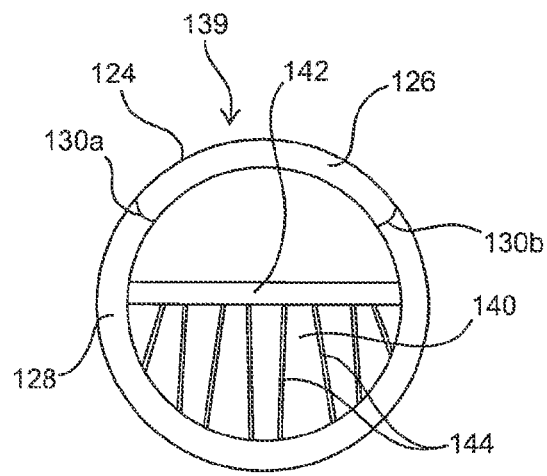

The restraining structure 140 of annuloplasty device 139 of FIG. 4C includes both a cross-restraint 142 generally along the horizontal axis and secondary restraints 144 situated generally along the vertical having a configuration and pattern similar to that of restraining structure 30 of annuloplasty device 20 of FIG. 2A. Here, again, primary restraint 142 is thicker than secondary restraints 144 but could also be of the same thickness material as the secondary restraints.

Figure 4D:
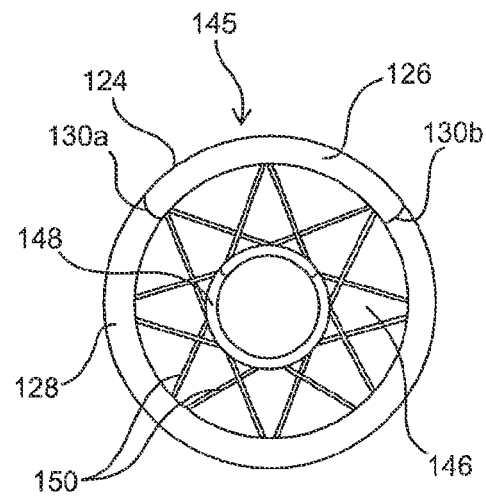

FIG. 4D illustrates an annuloplasty device 145 having a restraining structure 146 which is significantly different from the previously discussed restraining structures of the present invention. In particular, restraining structure 146 includes a primary or annular restraint 146 disposed concentrically within ring 124. While annular restraint 146 is positioned centrally in this embodiment, the annular restraint may be positioned at any suitable location within the interior of ring 124. A plurality of secondary or transverse restraints 150 extends across the area between annular restraint 146 and ring 124. Here, the various restraints form a star-like pattern and are each attached to the perimeter of annular restraint 146 as well as to ring 124 at two corresponding locations. Again, secondary restraints 150 are thinner than primary restraint 146. The inner ring provides an unobstructed central orifice for flow.

FIGS. 5A-D illustrate annuloplasty devices having an open ring configuration 152, and specifically a flexible C-shaped configuration wherein ring 152 is comprised only of a posterior segment. Surgeons who utilize flexible partial rings (bands) feel that the annular dilatation that occurs with mitral regurgitation is limited to the posterior portion of the annulus and, therefore, only this portion need to be attached to a ring to correct the annular dilatation. Annuloplasty device 154 of FIG. 5A has restraining structure 156 which includes curved cross-restraint 158 situated generally along a major axis of ring 152 and extending between junctures 155a, b of ring 152, and transverse restraints 160, extending between and affixed to cross-restraint 158 and ring or posterior segment 152. Similar to the configuration of transverse restraints 134 of FIG. 5A, secondary restraints 160 do not intersect each other within the interior of ring 124 and are not quite parallel to each other. Instead, secondary restraints 160 extend somewhat radially from cross-restraint 158 to posterior segment 152. Annuloplasty device 162 of FIG. 6B has restraining structure 164 having a curved primary restraint or cross-restraint 166 and angled secondary restraints 168. Cross-restraint 166 has a diameter that is thicker than those of the secondary restraints 168.

Figure 5A:
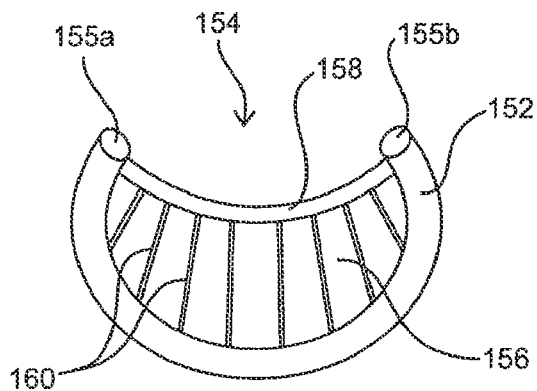
FIGS. 5A-D illustrate four exemplary embodiments of the annuloplasty device of the present invention having a C-shape, wherein the device of FIG. 5A has substantially parallel restraints extending between a cross-bar and the posterior segment of the ring; the device of FIG. 5B has zigzagging restraints extending between a cross-bar and the posterior segment of the ring; the device of FIG. 5C has intersecting restraints extending between a cross-bar and the posterior segment of the ring; and the device of 5D has intersecting restraints extending between the ring.
Figure 5B:
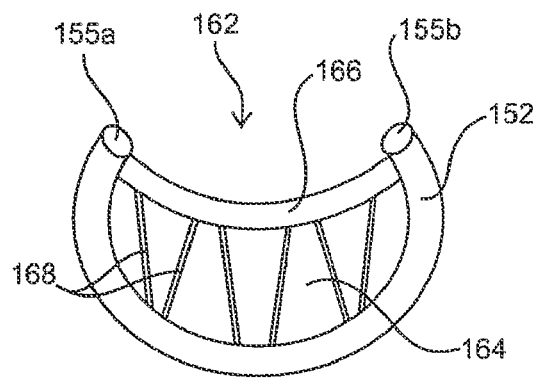
Figure 5C:
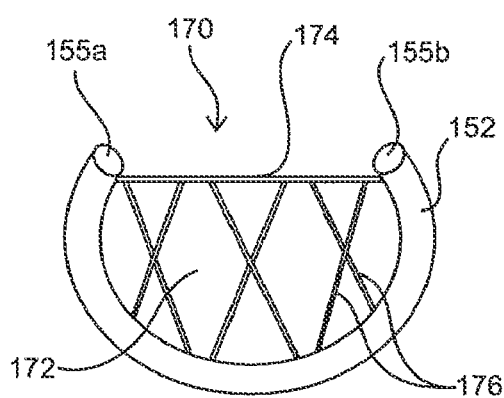

Annuloplasty device 170 of FIG. 5C has a restraining structure 172 having a straight primary restraint or cross-restraint 174 extending between distal ends 155 of ring 152. Six secondary restraints 176 form a crisscross pattern extending between ring 152 and primary restraint 174. Unlike various previously described embodiments of the annuloplasty device of the present invention, primary restraint 174 has substantially the same thickness or gauge as the secondary restraints 176.

Figure 5D:
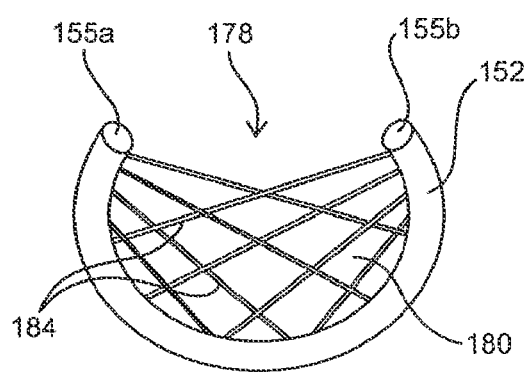

FIG. 5D illustrates yet another annuloplasty device 178 having restraining structure 180 which includes a plurality of same-diameter restraints 184. A first group of restraints 184 extend generally radially from respective points proximate left distal end 155a of ring 152 to corresponding respective points on the right side of ring 152. A second group of the restraints 184 extend generally radially from respective points proximate right distal end 155b of ring 152 to corresponding respective points on the left side of ring 152, thereby forming a web-like pattern with the first group of restraints 184. Any suitable number of groups of restraints may be employed with the annuloplasty devices of the present invention.

Figure 6A:
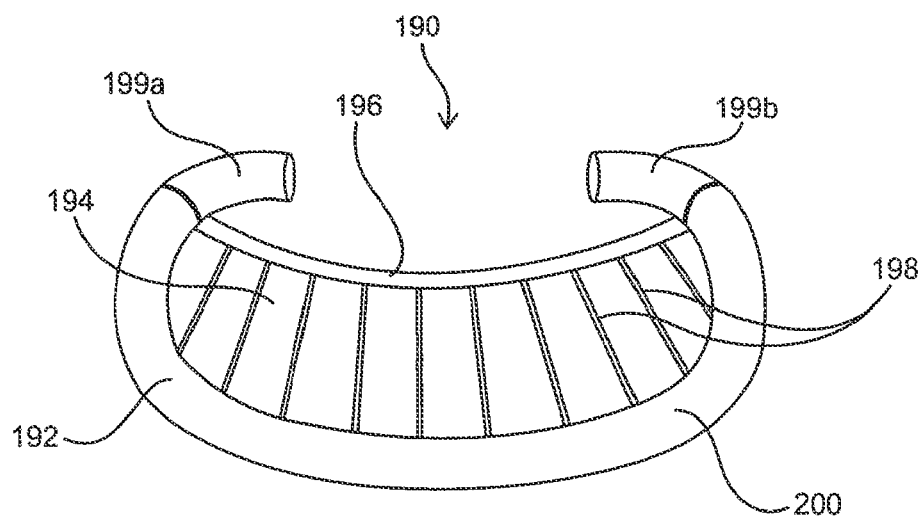
FIGS. 6A and 6B illustrate two exemplary embodiments of the annuloplasty device of the present invention having an open saddle shape, wherein FIG. 6A has substantially parallel restraints extending between a crossbar and the posterior segment of the ring.
Figure 6B:
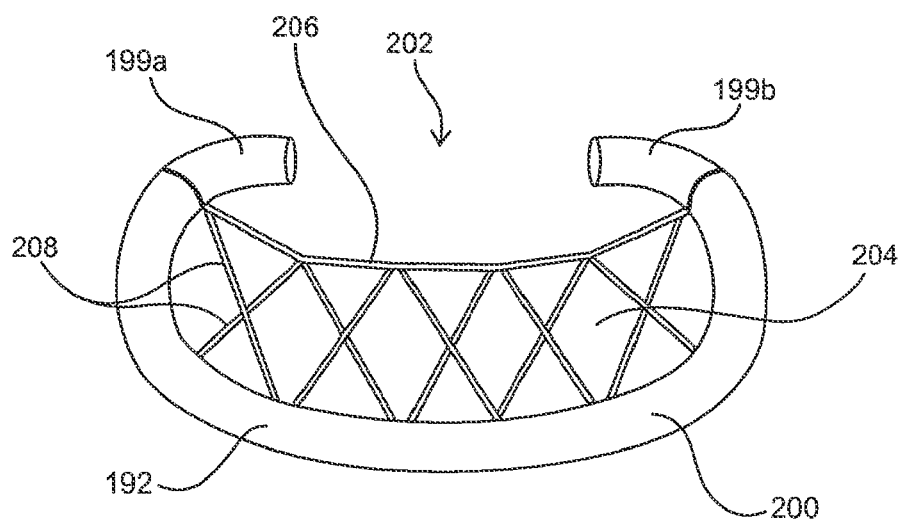

FIGS. 6A and 6B illustrate other annuloplasty devices 190 and 202, each having a semi-rigid, partial saddle-shaped annuloplasty ring 192, anterior segments 199a, 199b and posterior segment 200. Surgeons who prefer semi-rigid, partial rings also believe that the annuloplasty can be limited to the posterior annulus but feel that annular remodeling, fixing the anteroposterior dimension of the annulus as well as its circumference, is also important and can only be achieved with a non-flexible ring. Device 190 of FIG. 6A further includes restraining structure 194 having primary restraint 196, situated generally along the major axis of ring 192, and secondary restraints 198 extending radially from primary restraint 196 to posterior segment 202 generally along the minor axis of ring 192. Here, primary restraint 196 has a greater diameter than secondary restraints 198. Device 200 of FIG. 6B further includes restraining structure 204 having primary restraint 206 and transverse restraints 208 extending between primary restraint 206 and posterior segment 200 and forming a crisscross pattern. Here, primary restraint 206 has substantially the same diameter as secondary restraints 208.

Figure 7A:
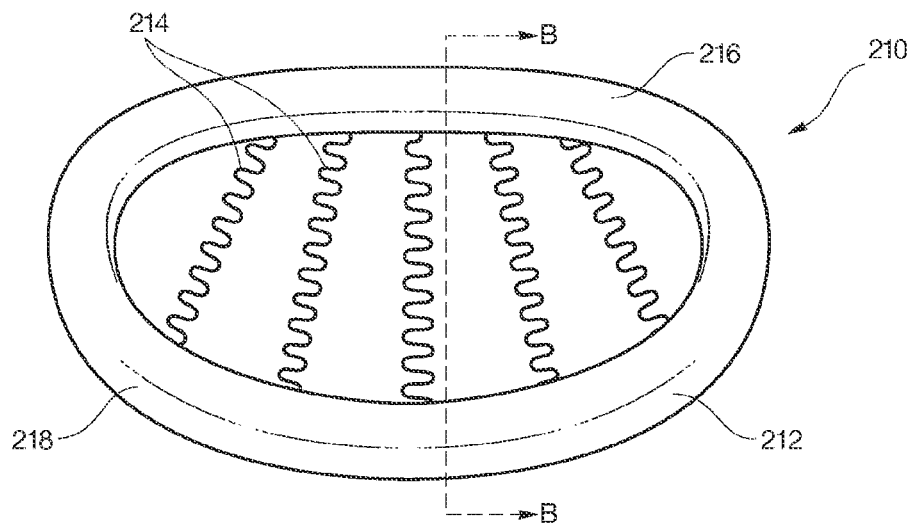
FIGS. 7A and 7B illustrate another annuloplasty device of the present invention having shock-absorbing leaflet restraint struts.
Figure 7B:
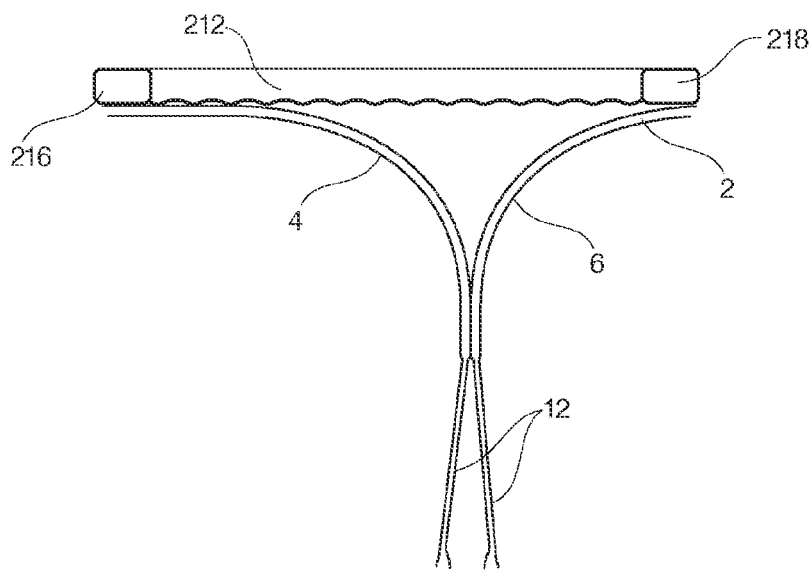
Figures 8A, 8B, 8C, 8D:
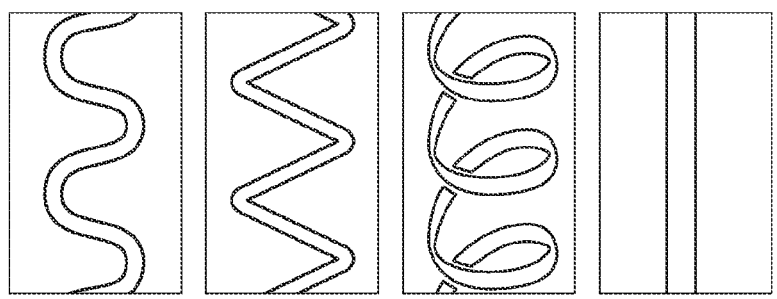
FIGS. 8A-D illustrate various designs and shapes of leaflet restraint struts which are suitable with the devices of the present invention.

FIGS. 7A and 7B illustrate another annuloplasty device 210 having D-shaped ring 212 and a plurality of cross-bars or struts 214 which extend slightly radially from the anterior side or portion 216 to a posterior side or portion 218 of ring 212. Here, struts 214 have a sinusoidal configuration (shown enlarged in FIG. 8A) which provide a wider leaflet restraining area than would a thinner straight strut but without much additional leaflet surface contact area or obstruction to blood flow. This may be accomplished with other suitable strut patterns including but not limited to those illustrated in FIG. 8, i.e., a zigzag pattern (FIG. 8B), a coiled or looping configuration (FIG. 8C) or a straight but wider ribbon configuration (FIG. 8D). Struts 214 may be attached to ring portions 216 and 218 at any suitable location along the inner diameter wall or surface (or may be attached on the bottom (leaflet-contact) surface). Here, struts 214 are shown attached closer to the ventricular or leaflet contacting side of ring 212 and extend substantially within a plane defined by the bottom surface of ring 232. As such, a substantial portion of the lengths of struts 214 are not in contact with the leaflet surfaces (as illustrated in FIG. 7B, which is a cross section of device 210 taken along the line b-b of FIG. 7A), except during systole at which they act to restrain prolapsing segments of one or more of the leaflets. As such, struts which have some elasticity are well suited for restraining leaflet motion in order to absorb the energy imposed on them by the leaflets and, in turn, dampen the impact on the leaflets which can minimize injury to the leaflet. Of course, the elasticity may be varied depending on the selection of materials. Suitable materials include nitinol covered in ePTFE, elastomers such as silicone and polyurethane, stainless steel wire with proper heat treating, and PET and UHMW polyethylene braided fibers. Also of note is that while ring 212 is shown having a square or rectangular cross-sectional shape, any suitable cross-sectional shape may be employed, including but not limited to oval, oblong (see FIG. 10B) circular, etc.

Figure 9A:
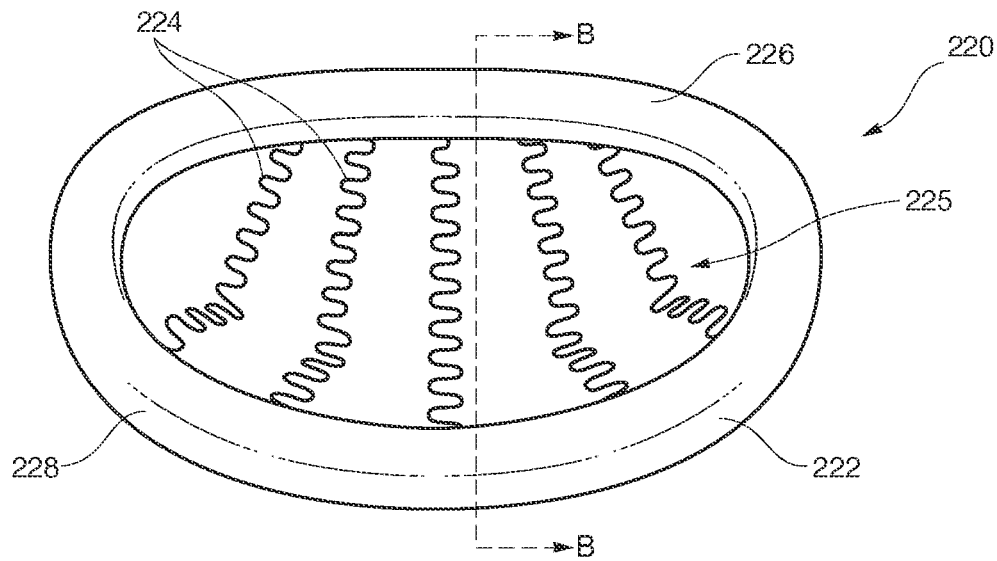
FIGS. 9A and 9B illustrate another annuloplasty device of the present invention having leaflet restraint struts which extend into the ventricle to facilitate correction of prolapse.
Figure 9B:
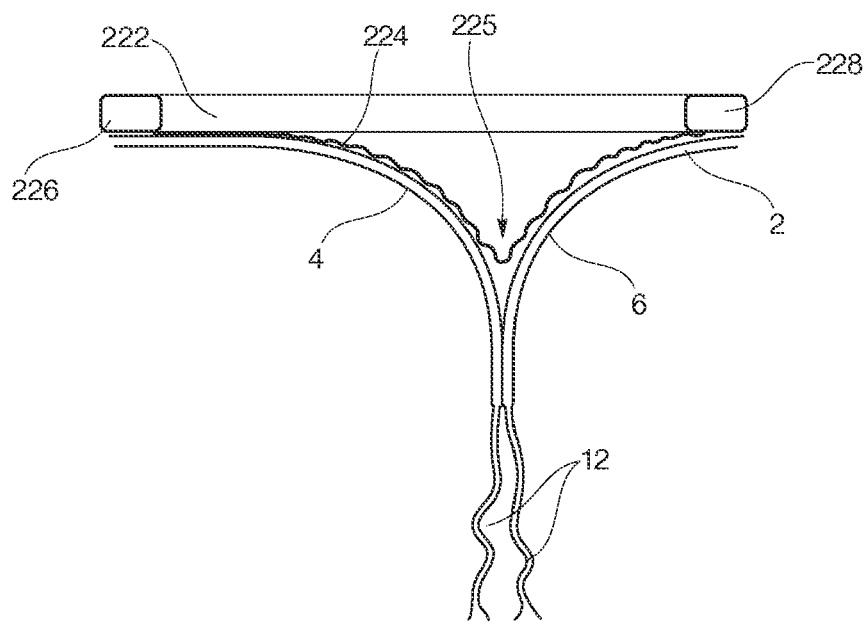

Annuloplasty device 220 of FIGS. 9A and 9B also employs struts 224 which are similar to those of FIGS. 7A and 7B, however, struts 224 extend below the plane defined by the underside of ring 222 and dip slightly into the ventricle in the vicinity of the expected line of coaptation. This dip permits the restraining struts to catch the prolapsing leaflet before it reaches the plane of the annulus. Since the surface of coaptation normally begins a short distance below the plane of the annulus, this dip or extension can assure that the leaflets begin to coapt before a prolapsing segment overrides a non-prolapsing segment. As best seen in FIG. 9B (which is provides a cross-sectional view of device 220 taken along the line b-b of FIG. 9A), struts 224 have a downward protruding bend 225 at the natural or desired line of coaptation between the leaflets, which is typically closer to the posterior side 228 of ring 222. However, the location of the bend relative to anterior side 226 and posterior side 228 may be varied to accommodate a particular repair application.

Figure 10A:
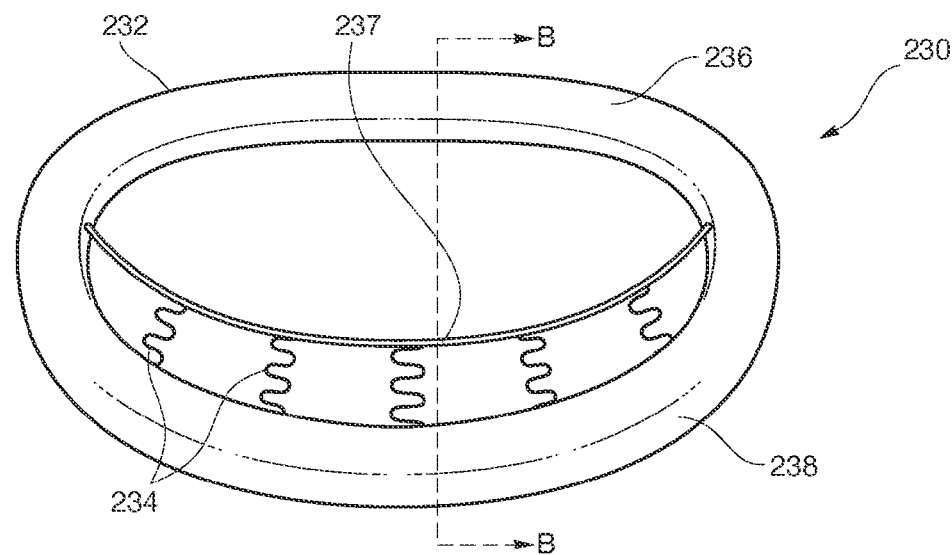
FIGS. 10A and 10B illustrate another annuloplasty device of the present invention having shock-absorbing leaflet restraint structure for treating prolapse limited to the posterior valve leaflet.
Figure 10B:
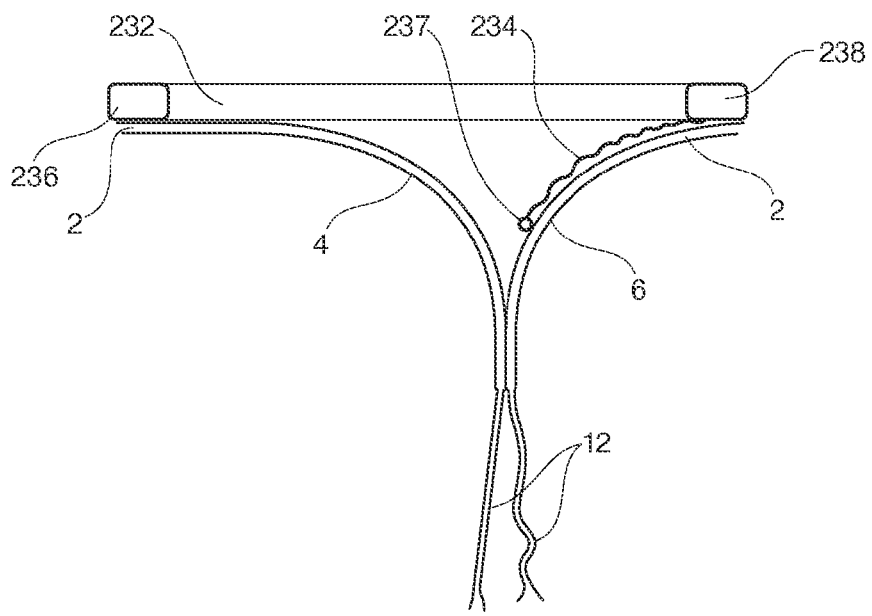

FIGS. 10A and 10B illustrates another annuloplasty device 230 having a restraining structure which occupies only a portion of the interior of ring 232. Here, the restraining structure extends over less than about half of the interior area of ring 232, and may extend to equal to or less than about ⅓ of the interior surface, such as in the illustrated embodiment. As such, the restraining structure, when operatively placed, extends over the posterior leaflet 6 but not the anterior leaflet 4, as shown in FIG. 9B. The restraining structure includes a primary restraining strut 237 and a plurality of cross-restraints 234 which extend between primary strut 237 and posterior portion 238 of ring 232. Primary strut 237 extends substantially along the major axis of the ring 232 and has a radius of curvature which restrains and positions the prolapsing segment of the posterior leaflet where it would be during systole in a normal valve, which in turn presents it to the non-prolapsing for coaptation. Cross-restraints 234 may have the same configuration and be made of the same material as the restraints of FIGS. 7-9. Like struts 224 of FIGS. 9A and 9B, primary strut 237 and cross-restraints 234 have a material length and configuration which allow them (whether preformed or conformable) to extend below the plane defined by the bottom surface of ring 232, and maintain contact with the leaflet surface through diastole. In another embodiment (not shown) primary restraint 237 could be omitted as long cross restraints 234 are individually stiff enough to hold their position during systole when the leaflet is snapping up against them.

As discussed above, rigid and semi-rigid rings are able to more completely and reliably remodel a valve and restore leaflet coaptation. However, flexible rings have the advantage of being somewhat easier to insert and secure to the annulus, and may more ably preserve the normal three dimensional "saddle" shape of the annulus and its complex motion during the cardiac cycle. The annuloplasty devices of FIGS. 11 and 12, while being flexible, provide the advantages of conventional rigid and semi-rigid annuloplasty rings in remodeling a valve having a dilated annulus. As the struts are positioned on the atrial side of the ring, they are not subject to make contact with the leaflet, and are present to fix the shape of the flexible ring, particularly the antero-posterior dimension which is critical to assuring proper leaflet coaptation.

Figure 11A:
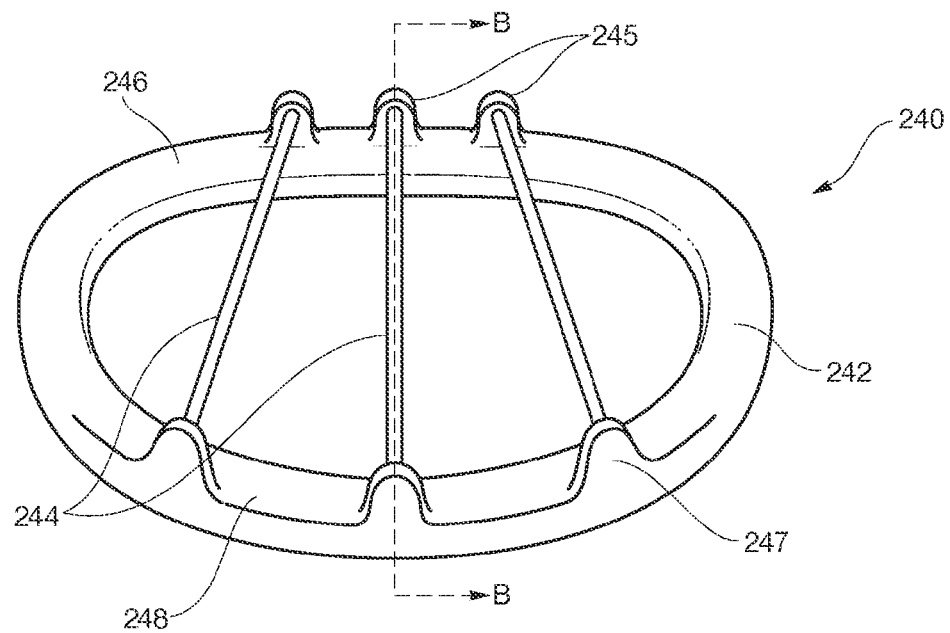
FIGS. 11A and 11B illustrate an annuloplasty device of the present invention for remodeling a valve annulus when leaflet prolapse is not present.
Figure 11B:
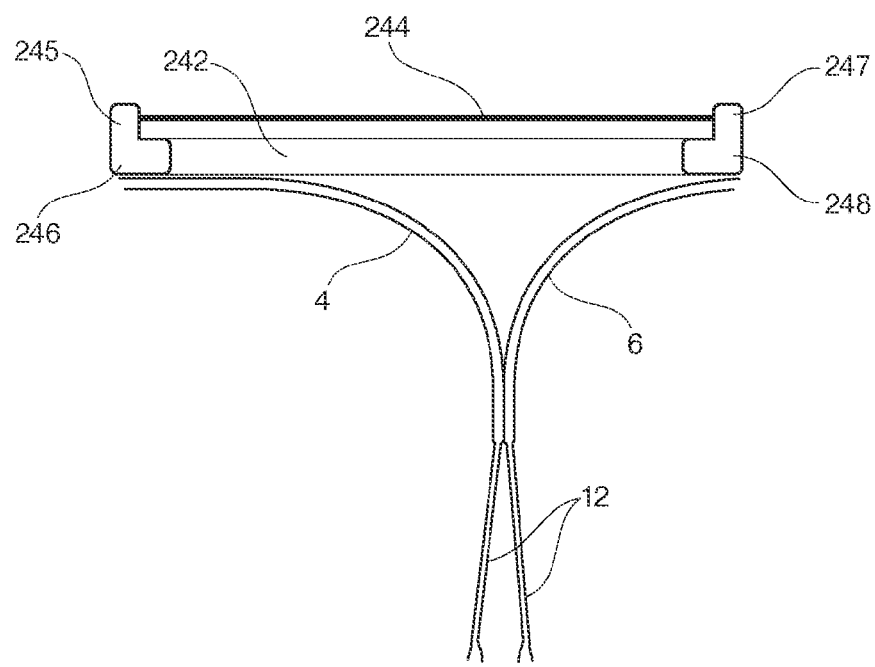

FIGS. 11A and 11B illustrate an annuloplasty device 240 having a flexible ring 242 and struts 244 extending from an anterior portion 246 to a posterior portion 248 of ring 242. Struts 224 are elevated above the top surface of ring 242 and are fixed thereto by mounts or mounting receptacles. Struts 244 are preferably inelastic (but may be flexible or rigid) so as to substantially maintain the diameter and shape of flexible ring 242 and, thus, maintain the remodeling characteristics imparted to a valve by device 240 throughout a valve's cycle of motion. Completely flexible struts would maximize the overall flexibility of the device while still remodeling the annulus. Suitable materials for the struts include nitinol covered in ePTFE or Dacron, elastomers such as silicone and polyurethane, stainless steel wire with proper heat treating, and PET and UHMW polyethylene braided fibers.

Each strut 244 is mounted by the attachment of one end to an anterior mounting receptacle 245 and the attachment of the other end to a corresponding posterior mounting receptacle 247. The mounts may be any suitable height so as to provide a vertical separation or lift-off between the struts and the ring where the struts reside above the plane defined by the top surface of ring 242, as is illustrated in FIG. 11B (which illustrates a cross-sectional view of device 240 taken along line b-b of FIG. 11A). Further, the mounts may be configured to allow the relative height of the struts to be adjustable. For example, where it is desirable to minimize contact with the leaflet surface, the struts may be adjusted upward, and visa-versa.

Figure 12A:
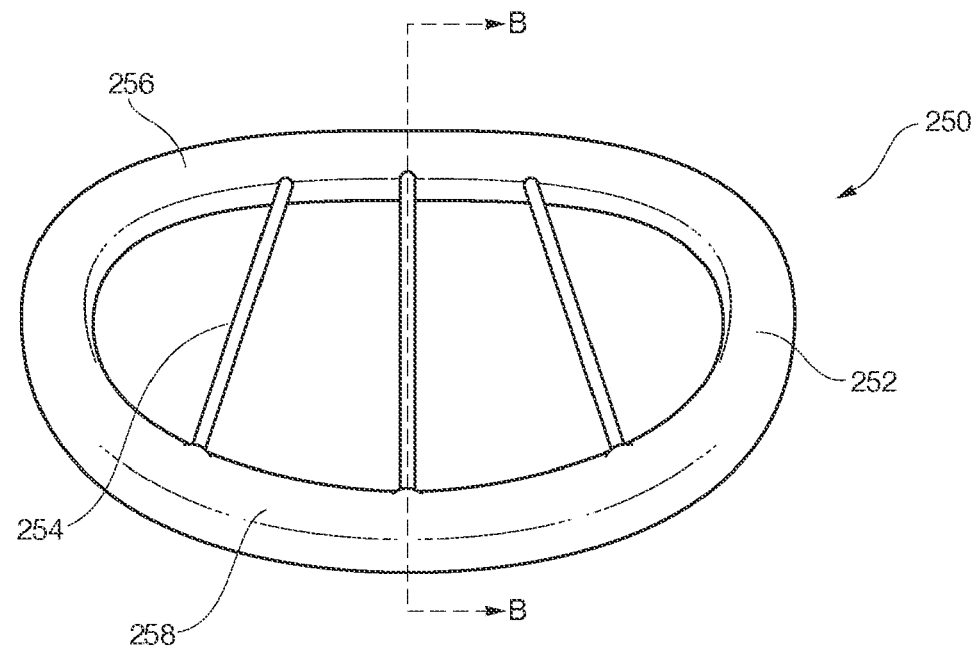
FIGS. 12A and 12B illustrate another annuloplasty device of the present invention for remodeling a valve annulus when leaflet prolapse is not present.
Figure 12B:
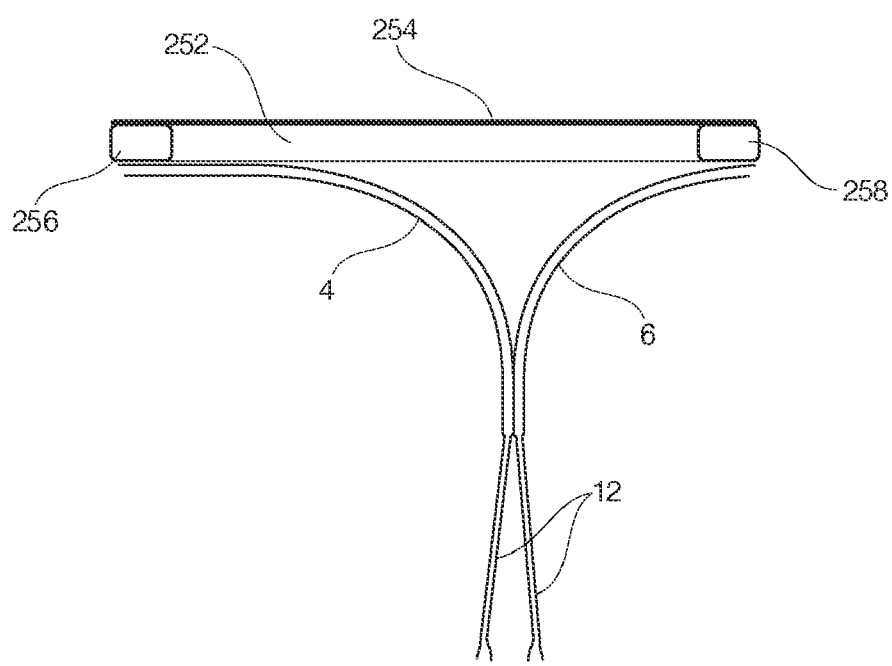

Annuloplasty device 250 of FIGS. 12A and 12B is similar in construct device 240 but its inelastic struts 254 are mounted closer to and more flush with the top surface of ring 252. With such a configuration, the number of struts 254 provided attached to ring 252 may be more than is required or necessary for a particular valve repair application. As such, those struts which are not necessary or inhibit the desired corrections to the valve may be removed either by being configured to be easily removed or released from ring 252 or by being cut from ring 252. In this way, the device may be customized for a particular application.

Figure 19:
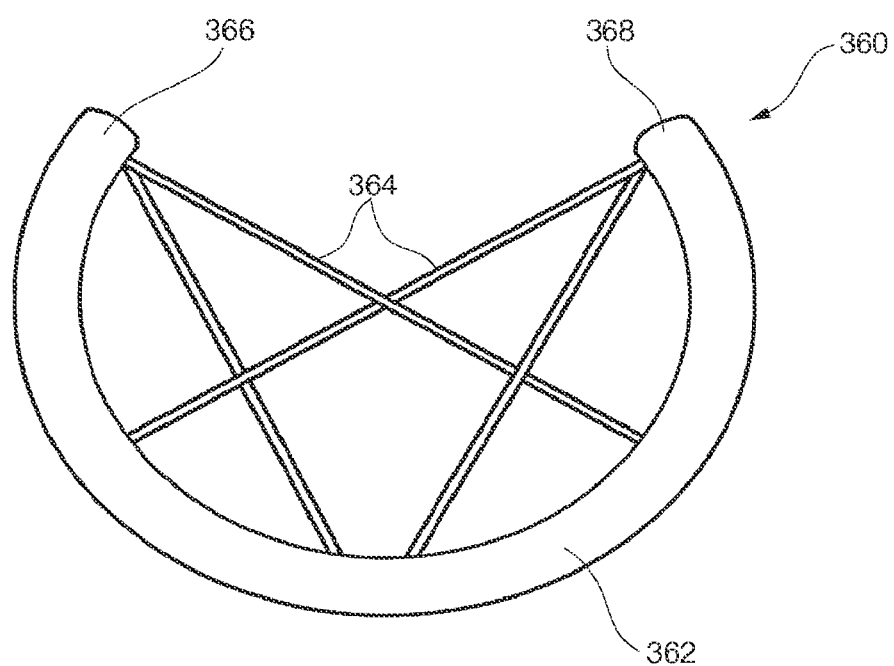
FIG. 19 illustrates an annupasty device of the present invention having a partial ring and criss-crossing remodeling struts.

Remodeling struts can be provided with partial rings as well. FIG. 19 illustrates such a device 360 having a partial ring 362 of substantial flexibility and cross-bars 364 extending in a criss-cross or star configuration between portions of ring 362. In particular, two remodeling struts emanate from each end of the ring and cross the ring orifice diagonally to the center and opposite portions, respectively, of the posterior portion of the ring, thereby providing a webbing structure.

Figure 13A:
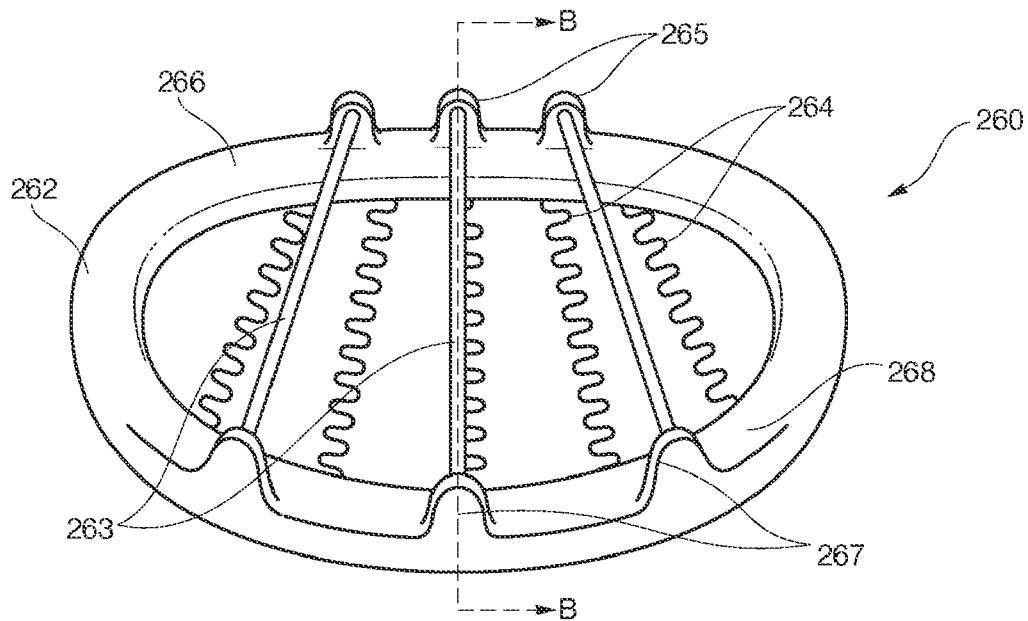
FIGS. 13A and 13B illustrate an annuloplasty device of the present invention having features for both restraining leaflet motion and remodeling a valve annulus.
Figure 13B:
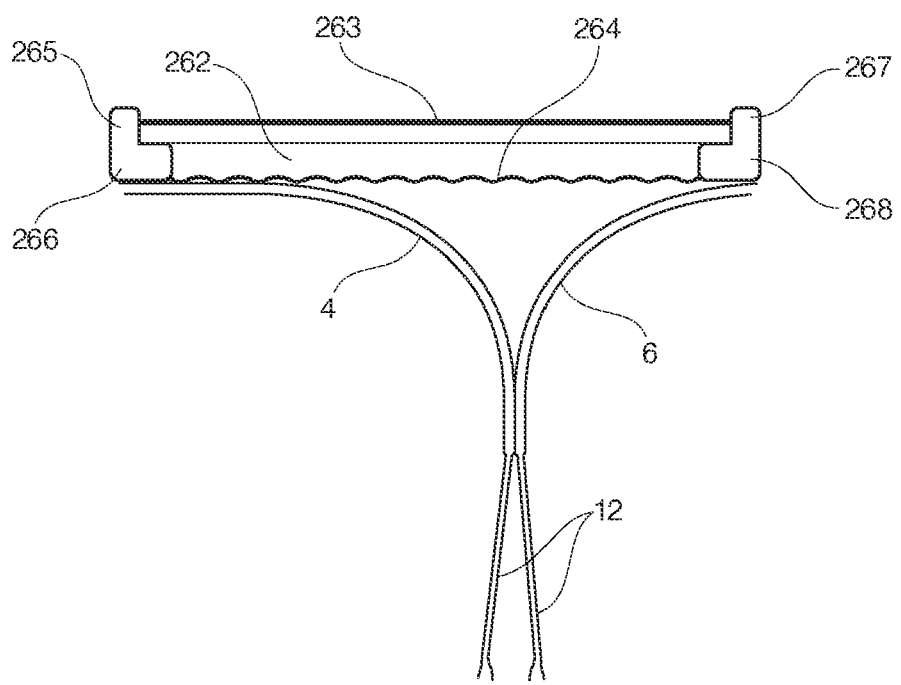
Figure 14A:
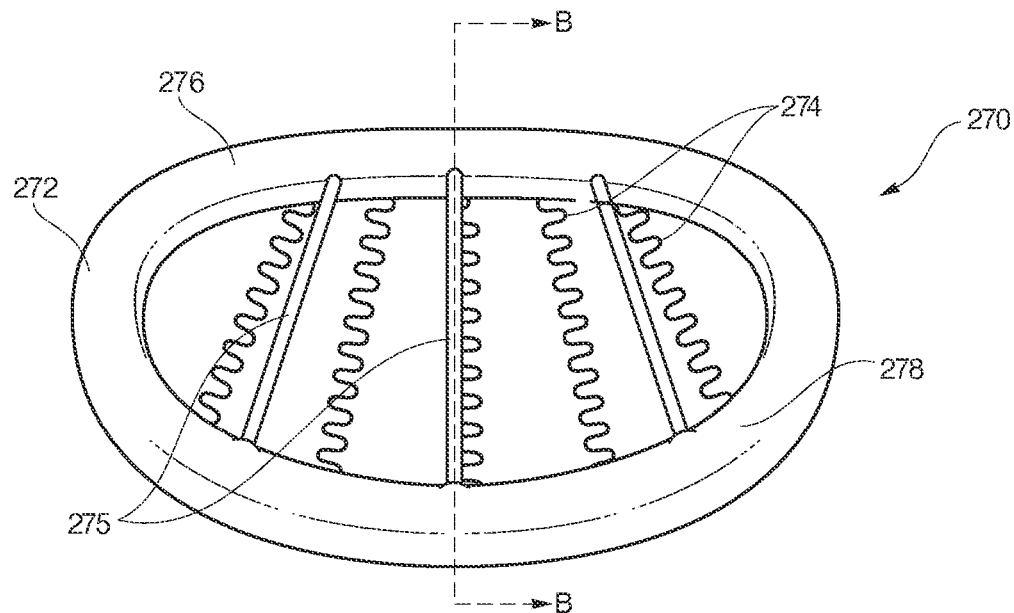
FIGS. 14A and 14B illustrate another annuloplasty device of the present invention having separate features for both restraining leaflet motion and remodeling a valve annulus.
Figure 14B:
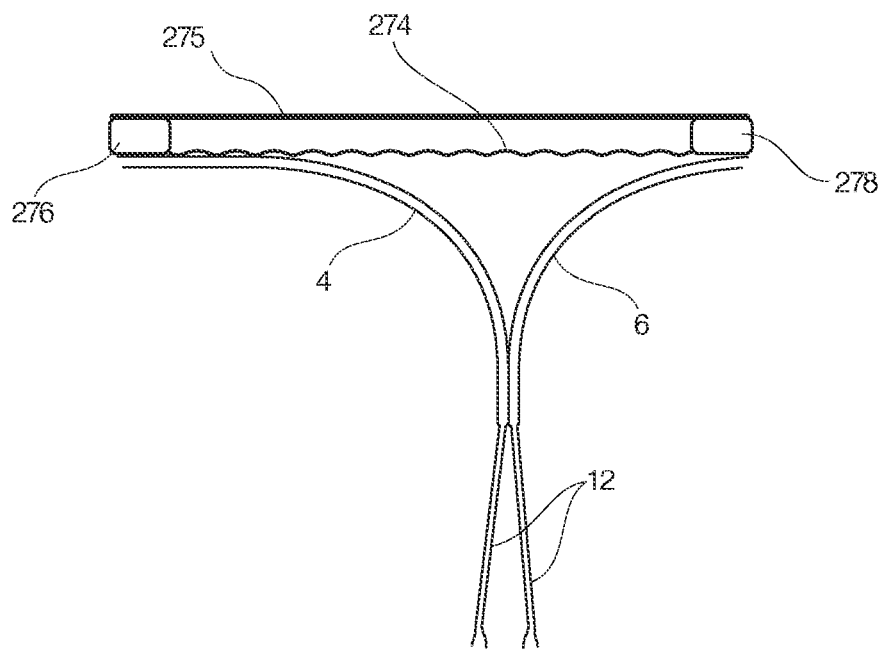
Figure 15A:
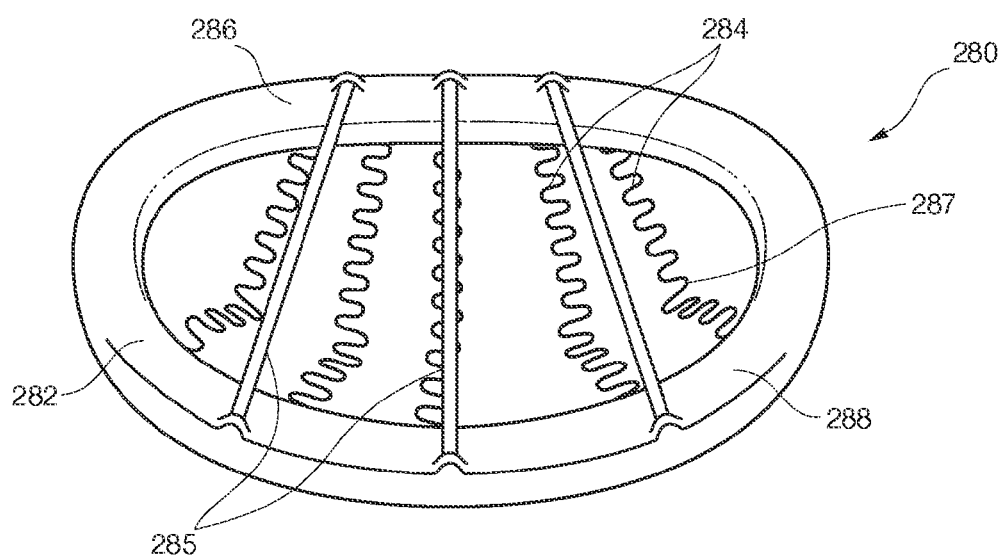
FIGS. 15A and 15B illustrate yet another annuloplasty device of the present invention having separate features for both restraining leaflet motion and remodeling a valve annulus.
Figure 15B:
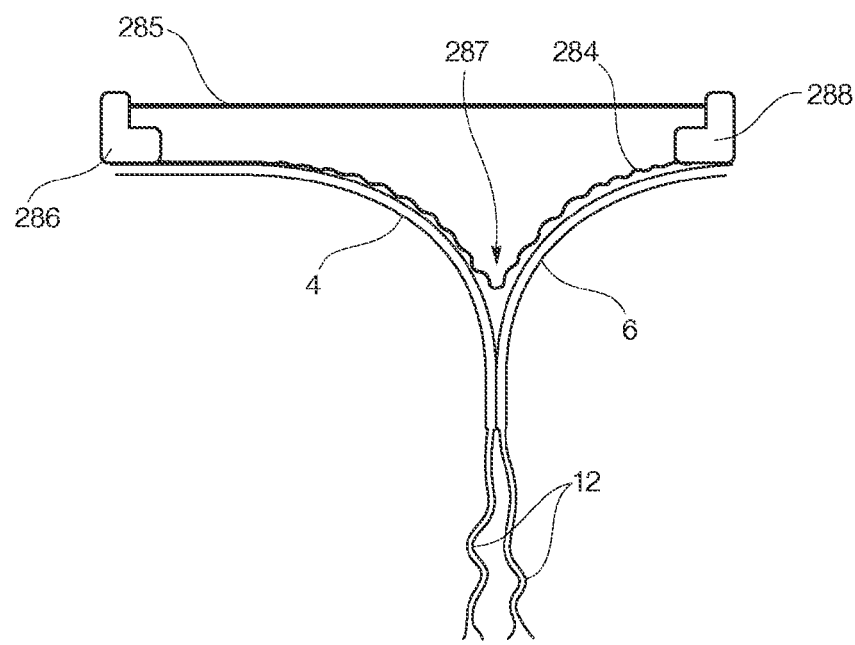

The present invention further includes annuloplasty devices which combine features directed to restraining leaflet prolapse and flexibly remodeling the valve annulus. Examples of such embodiments are illustrated in FIGS. 13-15 which employ various combinations of the remodeling struts and the restraining struts of the devices described above. For example, device 260 of FIGS. 13A and 13B includes a ring 262 having restraining struts 264 (similar to those of FIGS. 7A and 7B) extending across the interior of ring 262 substantially along a plane defined by the bottom surface of ring 262, and having remodeling struts 263 (similar to those of FIGS. 11A and 11B) extending across the interior of ring 262 substantially along a plane above the top surface of ring 262. Device 270 of FIGS. 14A and 14B includes a ring 272 having restraining struts 274 (similar to those of FIGS. 7A and 7B) extending across the interior of ring 272 substantially along a plane defined by the bottom surface of ring 272, and having remodeling struts 273 (similar to those of FIGS. 12A and 12B) extending across the interior of ring 272 substantially along a plane defined by the top surface of ring 272. Device 280 of FIGS. 15A and 15B includes a ring 282 having restraining struts 284 (similar to those of FIGS. 9A and 9B) extending across the interior of ring 282 substantially along a plane defined by the bottom surface of ring 282, and having remodeling struts 283 extending across the interior of ring 282 substantially along a plane above the top surface of ring 282.

While certain combinations of restraining and remodeling struts have been illustrated, any combination of struts and variations thereof may be used. For example, the restraining struts may be conformable or bent, and/or may cover the posterior leaflet only. Additionally, the remodeling struts may be malleable so as to place a bend, a bow or an arch in the strut in order to decrease the diameter or a portion of the diameter of a ring. Still yet, other means may be employed to adjust the length and shape of one or more struts to in turn adjust the diameter and/or shape of the ring. Certain of these means are illustrated in FIGS. 16-18.

Figure 16:
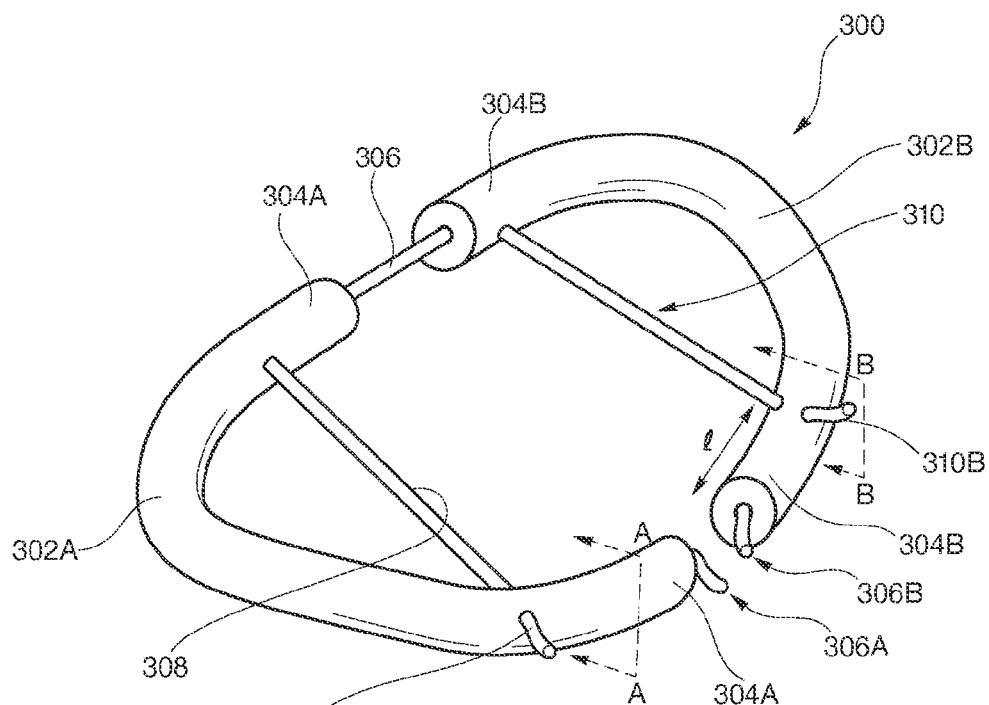
FIGS. 16, 16A and 16B illustrate an annuloplasty device of the present invention, the size and shape of which are adjustable after implantation.
Figure 16A:
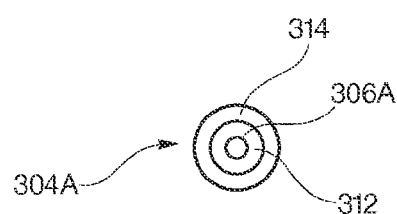
Figure 16B:
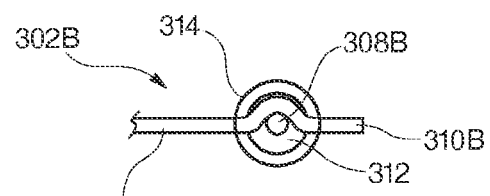

FIG. 16 illustrates a device 300 of the present invention having a two-piece ring where each piece 302a, 302b is flexible and has a crescent shape which are substantial mirror images of each other. The crescent pieces are interconnected by a thread chord 306 which extends through the core of each piece 302a, 302b, respectively, and extends from ends 304a, 304b, respectively. A cross-sectional view of end 304a is illustrated in FIG. 16A where chord 306a runs axially through a silicone tubing 312 having lubricous lumen to minimize friction on chord 306 as it is pulled through. Silicone tubing 312 is covered with a fabric, such as PTFE or PET, which functions as a sewing ring. Two other chords, strut chords are 308, 310, bridge the respective ends of pieces of 302a, 302b. The ends 304a of piece 302a are apposed with the ends 304b of piece 302b by pulling on the chord ends 306a, 306b. A cross-sectional view of ring piece 302b is illustrated in FIG. 16B, where strut chord 310 crosses perimeter reduction chord 308b. Subsequent to abutting the opposing piece ends, additional pulling of chord ends 306a and 306b results in compression of the pieces 302a, 302b along the major axis of the resulting ring. Similarly, pulling on chord ends 308a, 310b of strut chords 308, 310, respectively, results in compression pieces 302a, 302b along the minor axis of the resulting ring. The shortening or tensioning of the three chords is continued until the desired shape and size (perimeter reduction) of a complete ring is achieved. Upon achieving the desired configuration, the chord ends 306a, 306b, 308a 310b are fixed or tied to the pieces and trimmed to minimize excess exposed material. Various techniques and mechanisms may be employed to fix the respective chord ends such as stitching or crimping.

Figure 17:
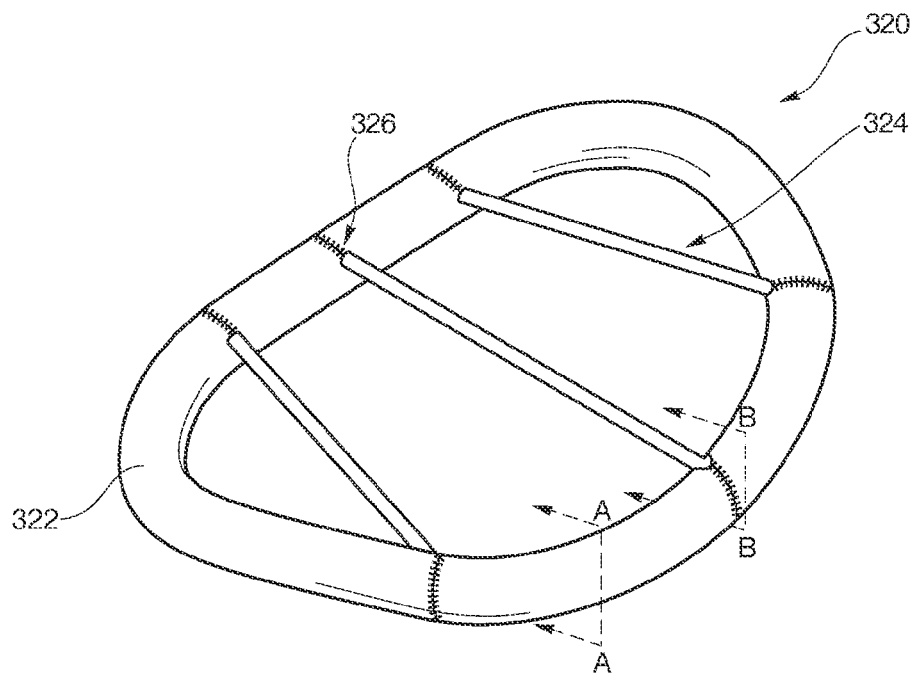
FIGS. 17 and 17A-E illustrate an annuloplasty device of the present invention having adjustable length struts and means for securing the struts to a ring.
Figure 17A:
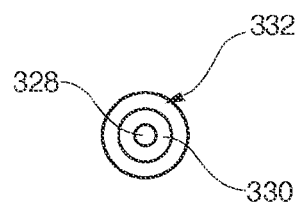
Figure 17B:
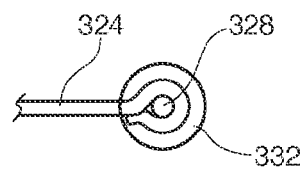
Figure 17D:
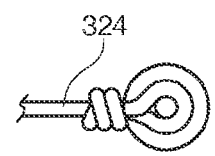
Figure 17C:
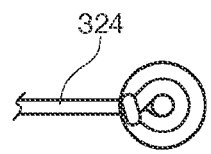
Figure 17E:
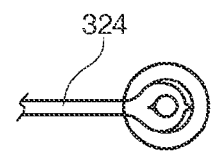
Figure 18:
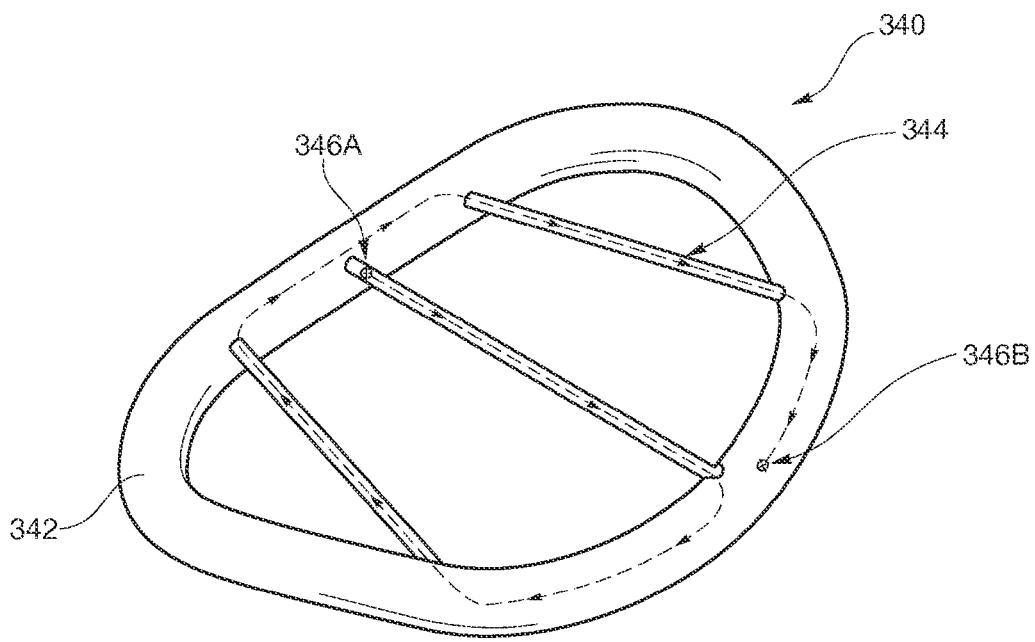
FIGS. 18, 18A-C illustrate another annuloplasty device of the present invention having adjustable length struts and means for securing the struts to a ring.

FIG. 17 illustrates a device 320 having a flexible ring 322 and adjustable length struts 324 extending transverse to the major axis of ring 322. A cross-sectional view of ring 322 at lines a-a is illustrated in FIG. 17A. Ring 322 includes a center core, made of PET, PE or ePTFE chord for example, within the lumen of silicone tubing 330. An outer fabric 332, such as PET or PTFE, covers tubing 330 and functions as a sewing ring. Struts 324 are made of nitinol with an elastic material. Struts 324 are selectively and individually pulled through ring 324 or, alternatively, the anterior and/or posterior sides are synched or compressed until a desired diameter along the minor axis is achieved. The struts are then fixed to the ring, which may be accomplished from a variety of techniques (shown in cross-section along lines b-b in FIG. 17) including but not limited to adhesion (FIG. 17B), crimping (FIG. 17C), knot tying, (FIG. 17D) or otherwise configured to be integrated or fixed to the core 328 of ring 322 (FIG. 17E).

As any means of terminating and fixing the struts to a ring may be time consuming and complex, the fewer the termination and fixation points, the less time consuming and the easier the procedure. FIG. 18 illustrates a device 340 which addresses this issue by a single chord 344 which provides a plurality of struts which bridge across the interior space of ring 342. Chord 344 has a length sufficient to extend along a path defined by the dashed arrows from a first termination point 346a to a second termination point 346b. Chord 344 is passed from within the core of ring 342 across the interior back into the core of ring 342 a desired number of times where each pass through creates a strut. The ring 342 has an internal construct so as to provide a pathway that allows translation of chord 344 without binding and bunching.

Figure 18A:
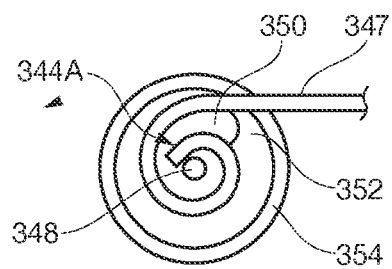
Figure 18B:
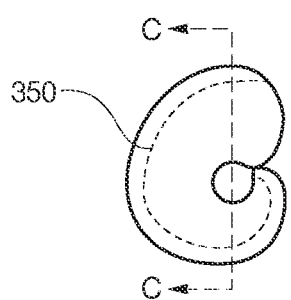
Figure 18C:
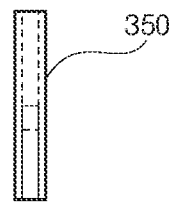

FIGS. 18A-C illustrate an exemplary internal construct of ring 342 where chord 344 is attached at an end 344a to a core 348, such as an ePTFE or PET chord, and is wrapped around a spacer 350 (detailed in FIGS. 18B and 18C, the latter showing a cross-sectional view of spacer 350 along line c-c in FIG. 18B) and a filler material 352. This assembly is covered by a fabric cover 354, which may act as a sewing cuff (e.g., PET fabric) for ring 342. Spacer 350 is preferably made from a preformed higher durometer silicone material and filler 352 is preferably made of a lower durometer silicone. Ring 342 is constructed by first retaining and winding chord 344 around spacer 350 and then placing the assembly in a preformed mold, i.e., filler material 352. The involute cross section of spacer 350 acts to uniformly stress-relieve the ring thereby minimizing fatigue failure of the assembly, while facilitating manufacturability.

Depending on the construct and materials used for a particular device of the present invention, a minimally invasive approach may be used to deliver and implant the devices at a valve site. The more flexible the overall configuration of a device, the more easily it can be reduced to a lower profile for delivery through a cannula or catheter to the target site. Such approaches, as described in greater detail below, include a catheter-based transeptal approach to the mitral valve, i.e., by way of the vena cava and right atrium and through the atrial septum into the left atrium. Another approach is by way of the aorta and into the coronary sinus approach without entering the cardiac chambers. FIGS. 20A-G illustrate a device which is deliverable by this latter approach.

The device consists of a partial annuloplasty band or segment having a length and diameter and made of a material to reside in the coronary sinus. The coronary sinus, which is the final vein draining the myocardium courses in the atrioventricular groove in close proximity to the mitral annulus before draining into the right atrium. As such, structures placed in the coronary sinus can be utilized to constrict and reshape the mitral annulus. This device further includes one or more struts that are deployable from the band or segment once placed within the coronary sinus. The struts are configured to penetrate the coronary sinus wall and extend across a desired portion of the surface of one or more of the leaflets. The struts are preferably made of a shaped memory material such as Nitinol whereby they are fabricated with a preformed configuration directed to treating the particular anomaly of the valve being repaired. For example, some or all of the struts may have a selected length and a preformed curve or bend which. The struts may have the same or varying lengths and extend over, short of or just to the line of coaptation between the leaflets. In the illustrated embodiment, the struts, when deployed from the coronary sinus and operatively positioned at the valve, extend over the posterior leaflet and particularly over the prolapsing segment(s) and curve downward toward the ventricle.

Figure 20A:
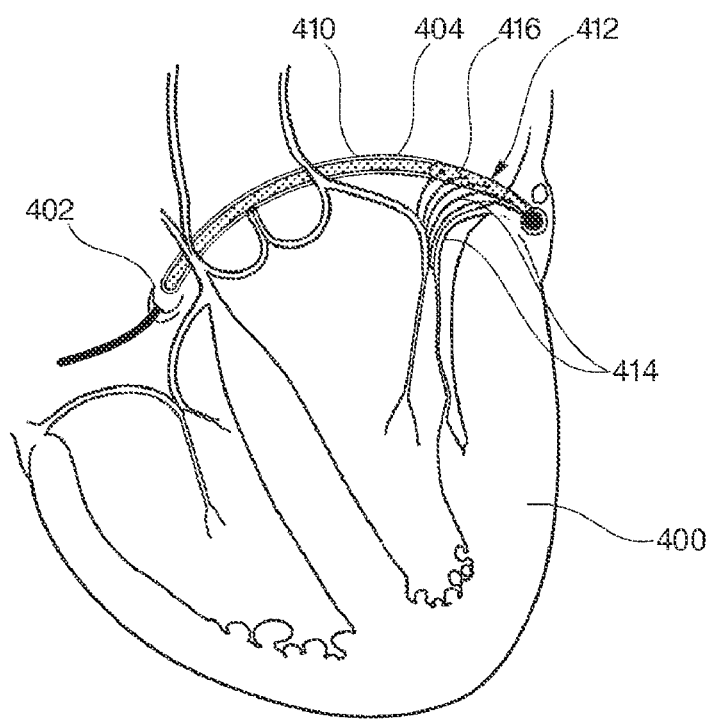
FIGS. 20 A-G illustrate another annuloplasty device of the present invention which can be deployed percutaneously using guidewires and catheters through the coronary smus.
Figure 20F:
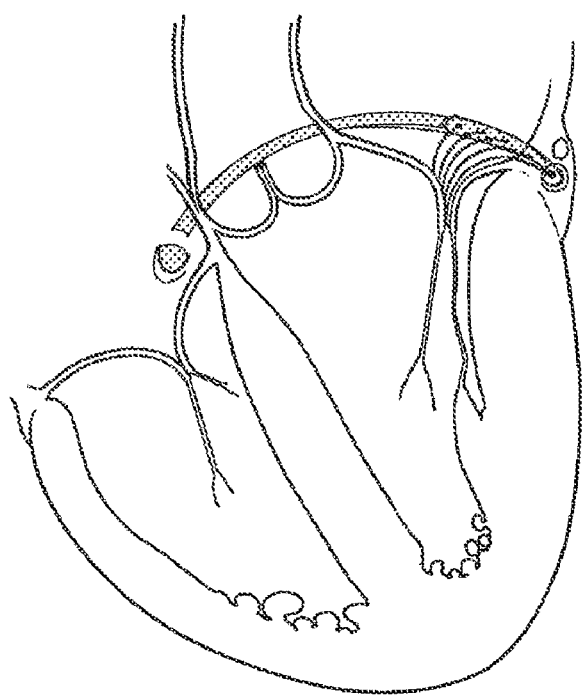

Referring now to FIG. 20A, a schematic illustration is provided of heart 400 having a coronary sinus opening 402 in the right atrium. An annuloplasty device 412 is releasably attached to the distal end of a delivery catheter 410 which has been delivered into the coronary sinus 404. Device 412 includes a partial ring, band or segment 416 which contains a plurality of struts 414. A corresponding plurality of openings 420 are provided along a side of band 416 through which one (or possibly more) struts is deployable. Band 416 may be rigid and selectively shaped so as to manipulate the valve annulus as desired to remodel the annulus. Alternatively, particularly where the annulus does not require remodeling, band 416 may be flexible and conform to the natural configuration of the annulus.

Catheter 410 is provided with member (not shown) which can advance the struts such that they are translated and exited from openings 420. Upon exiting form the openings, the struts penetrate the wall of the coronary sinus at the left atrium. Further advancement extends the struts over the posterior leaflet 422 of mitral valve 418 and towards the left ventricle, thereby restraining the prolapsing segment(s) of the leaflet. The struts 414 are shown being individually deployed through multiple separate openings within the band 416, however, they may be simultaneously deployed through a single opening or a number of openings less than the number of struts. Fluoroscopic markers or other image guidance mechanisms may be employed on band 416 to allow accurate placement of the band within the coronary sinus and alignment of the openings such that struts 414 penetrate the valve space at a desired location and angle. Once band 416 is in position and the struts deployed, the device can be detached from the catheter 410.

While a number of exemplary embodiments have been particularly described, those skilled in the art of cardiac valve repair will appreciate that an unlimited number of device configurations is within the scope of the present invention. The suitability of a particular device configuration, ring configuration, and restraining and/or remodeling structure configuration (if any), and the numerous permutations thereof, will depend on the particularities of the indication(s) being treated and the particular biases of the implanting surgeon. In other words, any suitable ring shape, contouring, size and thickness may be employed with any suitable restraining and/or remodeling structure configuration (if any) including, any suitable number, spacing, length, thickness, relative positioning and attachment means of the individual restraint or remodeling members being employed.

More particularly, the rings of the present invention may have shapes which are closed or open, including but not limited to D-configurations, circular configurations, C configurations or saddle configurations. The rings may be planar, substantially planar or non-planar, i.e., have contouring in the shape of a saddle. A full range of ring sizes can be available to accommodate all adult and pediatric dimensions. The range of horizontal diameters could extend from about 16 to about 44 millimeters but may be longer or shorter. For semi-rigid rings the ratio of the horizontal diameter to vertical diameter could extend from approximately 2.5:1 (e.g., FIG. 6A-B) to 3:2 (e.g., FIG. 3A-D) to as low as 1:1.

The primary or cross-restraints or remodeling struts of the present invention may have straight (e.g., FIGS. 4C and 5C), or bowed or curved (e.g., FIGS. 2A, 3A, 3B, 5A, 5B, 6A and 6B) configurations. The primary restraints may curve either towards the posterior segment or the anterior segment of the annuloplasty ring. They can be flexible, semi-rigid or rigid. They can be elastic or non-elastic. They can have a string or bar-like structure with a circular cross-section or be flat and ribbon-like. The primary restraints or struts may have thicknesses that are the same as, greater than or less than the ring itself although generally they would with a diameter ranging from about 0.2 to about 5 millimeters depending on the configuration.

The secondary or transverse restraints or struts may have the same lengths (e.g., FIG. 4D), substantially the same lengths (e.g., FIGS. 3A, 5A-C, 6A and 6B) or varying lengths (e.g., FIGS. 2A, 3A, 3B and 3D, 4A, 4C and 5D). Transverse restraints or struts may be parallel (e.g., FIG. 3D), angled (e.g., FIGS. 2A, 4A, 4C, 5A, 5B and 6A) to each other or non-parallel forming zigzag (FIGS. 3A and 4B), crisscross (e.g., FIGS. 3B, 3C, 4C, 5C, 6B and 8), star-like (e.g., FIG. 4D), web-like (e.g., FIG. 5D) or radial patterns (e.g., FIGS. 4A, 5A and 6A) or the like. The thicknesses of the restraints or struts may be identical to each other (e.g., FIGS. 3C, 3D, 4A, 4B, 5C, 5D and 6B) or vary from restraint to restraint, e.g., the primary restraint (e.g., cross-restraint and annular restraint) or struts may be thicker than the secondary or transverse restraints (e.g., FIGS. 2A, 3B, 3D, 4A, 4B, 5A, 5B and 6A) or visa-versa. They can be flexible, semi-rigid or rigid. They can be elastic or non-elastic. They can have a string or bar-like structure with a circular cross-section or be flat and ribbon-like. The primary restraints or struts may have thicknesses that are the same as, greater than or less than the ring itself although generally they would with a diameter ranging from about 0.2 to about 5 millimeters depending on the configuration.

As mentioned above, the positioning of the secondary or transverse restraints or struts with respect to the primary cross-restraint or strut and/or the ring of the annuloplasty devices of the present invention may vary and include an indefinite number of particular configurations. The transverse restraints or struts may be parallel with each other or non-parallel, forming an angle at the point of intersection or attachment of a transverse restraint or strut with the ring and/or with a cross-restraint or strut. Generally, these angles range from about 45° to about 90°, typically from about 60° to about 90°, and more typically from about 80° to about 90°. The secondary or transverse restraints or struts may have the same or varying lengths depending on the respective locations of corresponding points of attachment to the ring and/or cross-restraint. Also, the distances between adjacent transverse restraints or struts may be equally spaced or may vary from one to the next. Any suitable number of transverse restraints or struts may be employed with the rings of the present invention. Typically, 3 to 15 transverse restraints or struts are used, and more typically 6 to 10 are employed; however, only 1 or more than 15 may be employed.

The rings of the present invention consist of an inner frame made of metal, such as stainless steel or titanium, or of a flexible material, such as silicone rubber or Dacron cordage. The inner frame is covered with a biocompatible fabric or cloth such as Dacron, polytetraflourethylene (PTFE), which must allow a needle to penetrate, hold a suture and promotes tissue ingrowths and healing. The rings may be rigid, semi-rigid or flexible. The cross- or transverse restraints or struts (if any) may be made of any of the material with which the outer ring can be made or any biocompatible, non-absorbable suture-like material such as PTFE, polypropylene, polyester and nickel-titanium. The restraints or struts may be rigid, semi-rigid or flexible, and may be elastic or inelastic, and may be cord-like or ribbon-like. Additionally, they may be contiguous with (i.e., extensions of) the covering of the ring or may be attached to it in a secure fashion such as a knot, loop or other connection as described above.

The various methods of the present invention for using the subject devices and for repairing cardiac valves will now be discussed in detail. The following subject methods will primarily be described in the context of repairing a mitral valve in a conventional fashion through a full sternotomy. However, those skilled in the art will understand the necessary modifications to the procedure in order to access and repair the other cardiac valves through standard or less invasive approaches.

After prepping and placing the patient under anesthesia, an intra-operative transesophageal echocardiogram (TEE) is usually performed to assess the heart and valves. A careful assessment of the location and type of dysfunction on the TEE can be critical in planning the appropriate surgical procedure and annuloplasty device. It can accurately predict the need for adjunctive procedures to the leaflets and subvalvular apparatus in addition to the annuloplasty device which can in turn determine whether a minimally invasive approach is advisable. A surgical incision is then made in the patient's chest. The conventional, and still most common, approach would be through a full median sternotomy. Other less invasive approaches include a partial sternotomy and a right (or less frequently left) full, partial or "mini" thoracotomy. Mitral valve repair procedures using the present invention would likely be more amenable to these less invasive approaches as the need for complex adjunctive procedures beyond annuloplasty device insertion will be eliminated or minimized.

Cardiopulmonary bypass is then established, typically by inserting cannulae into the superior and inferior vena cavae for venous drainage and into the ascending aorta for arterial perfusion. The cannulae are connected to a heart-lung machine which oxygenates the venous blood and pumps it into the arterial circulation. Additional catheters are usually inserted to deliver "cardioplegia" solution, which is infused into the heart after isolating it from the circulation with a clamp on the aorta and stop it from beating. Numerous modifications of this basic technique are possible, commonly used, especially in minimally invasive procedures, and are understood by those skilled in the art of cardiac surgery. Once cardiopulmonary bypass and cardiac standstill have been achieved, the mitral valve is exposed by entering the left atrium and retracting the atrial tissue away using sutures or retraction devices. The atriotomy (entry incision) is usually made in the right side of the left atrium, anterior to the right pulmonary veins, although other approaches are occasionally used, especially in minimally invasive procedures.

Once good exposure of the mitral valve has been achieved, a careful valve analysis or "interrogation" is performed. Each segment of each leaflet is carefully assessed using special forceps and hooks to determine its pliability, integrity and motion. Based on this assessment, the surgeon determines whether the valve can be repaired or must be replaced. A successful valve repair is considered very likely as long as the leaflets have an adequate amount of pliable (non-calcified) tissue. The leaflet motion is then classified according to Carpentier's classification as Type I valve dysfunction (normal), Type II valve dysfunction (leaflet prolapse) or Type III valve dysfunction (restricted leaflet motion) and, based on this classification, the necessary steps of the repair are determined. In patients with Type I or IIIB valve dysfunction, the repair can nearly always be achieved with insertion of an appropriately sized (true-sized for Type I valve dysfunction and down-sized for Type IIIB valve dysfunction) remodeling annuloplasty ring alone. With conventional annuloplasty rings, however, patients with Type II or IIIA valve dysfunction usually require extensive, adjunctive procedures such as multiple leaflet resections and chordal transfers in Type II valve dysfunction or leaflet extension and chordal resection in Type IIIB valve dysfunction.

With the annuloplasty devices of the present invention, many if not most patients will not require any adjunctive procedures since the net-like restraining structure of the device will correct any prolapse by preventing the dysfunctional segment from rising above the plan of the annulus into the left atrium. In selected patients the surgeon may choose to perform limited adjunctive procedures prior to implanting the annuloplasty device; however the number and complexity of these procedures will be significantly less than in conventional mitral valve repair. For example, for Type I dysfunctions, a remodeling annuloplasty device may be used alone without any adjunctive procedures. On the other hand, where a valve suffering from Type II dysfunction is noted to have a large redundant prolapsing segment of the posterior leaflet, the surgeon may choose to perform a limited resection of the redundant posterior leaflet prior to implanting the device to prevent this excess tissue from obstructing flow within the left ventricle. With devices of the present invention, however, the surgeon can ignore residual prolapse of either leaflet and would not need to perform any complex adjunctive procedure such as a sliding valvuloplasty of the posterior leaflet or any procedure on the anterior leaflet. In a patient with Type IIIA disease (restricted leaflet motion usually due to fibrosis from rheumatic heart disease), the surgeon may choose to resect multiple restricted chordae to either leaflet to improve their mobility without having to worry about correcting any resulting leaflet prolapse.

The implantation of the annuloplasty devices of the present invention is very similar to that of conventional annuloplasty rings. Any implantation technique currently utilized for annuloplasty ring implantation can be applied to the current device including, but not limited to, interrupted mattress sutures, a continuous running suture, interrupted simple (non-mattress) sutures, specialized clips or staples. The most common method uses a plurality (typically 6-15) of non-pledgeted horizontal mattress sutures made from a braided, non-absorbable material such as polyester. Successive suture bites are taken deep into the fibrous substance of the annulus in a tangential direction around its circumference. Complete rings require sutures extending around the complete circumference of the annulus. Partial rings, on the other hand, typically terminate just inside each commisure (a dimple known as the "trigone") and thus do not require placement of sutures along the anterior annulus. The commissural marks on the ring allow the sutures to be properly aligned and ring to be properly oriented within the annulus. Typically all of sutures are placed in the annulus and then through the fabric of the annuloplasty ring before being tied and cut. Alternatively the sutures can be placed into the ring after each bite, a technique that can facilitate minimally invasive implantation. It is not necessary to suture any of the restraining members, either the primary or secondary restraints, to the valve.

Once the sutures are tied and cut, the repaired valve is tested to confirm a good line of coaptation without residual regurgitation. This is typically performed by injecting saline into the left ventricle until sufficient pressure develops to close the leaflets. Once the valve repair is complete the atriotomy incisions are closed, the entrapped air is removed from the heart, the cross clamp is removed and the heart is reperfused causing it to start beating again. Soon there after the patient is gradually weaned off the support of the heart lung machine. The repaired valve is assessed using the transesophageal echocardiogram. If the repair is satisfactory, the cannulae are removed and the incisions are closed in a fashion consistent with other cardiac surgical procedures.

Also provided by the subject invention are kits for use in practicing the subject methods. The kits of the subject invention include at least one subject annuloplasty device of the present invention. Certain kits may include several subject annuloplasty devices having different ring sizes, shapes and/or restraining structure configurations. Additionally, the kits many include certain accessories such as an annulus sizer, a ring holder, suturing devices and/or sutures. Finally, the kits may include instructions for using the subject devices in the repair of cardiac valves, particularly the mitral and tricuspid valves. The instructions for use may include, for example, language instructing or suggesting to the user the most appropriate ring shape and/or type of restraining configuration for treating a particular indication. These instructions may be present on one or more of the packaging, a label insert, or containers present in the kits, and the like.

It is evident from the above description that the features of the subject annuloplasty devices and methods overcome many of the disadvantages of prior art annuloplasty rings and valve repair procedures including, but not limited to, minimizing the number or adjunctive procedures and instruments necessary to completely repair a cardiac valve, simplifying the repair procedure allowing more surgeons to offer this procedure to their patients and facilitating minimally invasive approaches to valve repair. As such, the subject invention represents a significant contribution to the field of cardiac valve repair.

While the present invention has been described with reference to the specific embodiments thereof, it should be understood by those skilled in the art that various changes may be made and equivalents may be substituted without departing from the true spirit and scope of the invention. In addition, many modifications may be made to adapt to a particular indication, material, and composition of matter, process, process step or steps, while achieving the objectives, spirit and scope of the present invention. All such modifications are intended to be within the scope of the claims appended hereto.

What is claimed is:

1. An implantable device for repairing a mitral valve having an annulus, multiple leaflets and a subvalvular apparatus, comprising:
   a band configured for placement in a coronary sinus adjacent to the valve annulus, and having an interior pathway within at least a portion of the band;
   a plurality of openings positioned along a side of the band in spaced relation to one another, the openings being in communication with the interior pathway; and
   at least one restraining strut extending from within the interior pathway of the band through at least one of the openings in a substantially transverse orientation with respect to the band and shaped to extend from at least one of the openings, through the coronary sinus wall, over a leaflet of the mitral valve and toward the left ventricle to restrain prolapsing of the valve leaflet.

2. The device of claim 1 wherein said at least one strut is configured to restrain the abnormal motion of at least a portion of at least one valve leaflet.

3. The device of claim 2 wherein said at least one strut is configured to contact a portion of at least one valve leaflet.

4. The device of claim 3 wherein said contact portion of said leaflet is a prolapsing segment.

5. An implantable device for repairing a mitral valve having an annulus, multiple leaflets and a subvalvular apparatus, comprising:
   a band configured for placement in a coronary sinus adjacent to the valve annulus, and having an interior pathway within at least a portion of the band;
   a plurality of openings positioned along a side of the band in spaced relation to one another, the openings being in communication with the interior pathway; and
   at least one flexible restraining strut extending from within the interior pathway of the band through at least one of the openings in a substantially transverse orientation with respect to the band and shaped to extend from at least one of the openings, through the coronary sinus wall, over a leaflet of the mitral valve and toward the left ventricle to restrain prolapsing of the valve leaflet.

6. The device of claim 5, wherein the flexible strut is designed for engaging the valve leaflet.

7. The device of claim 6, wherein the strut includes a preformed curve for engaging the valve leaflet.

* * * * *